(12) United States Patent
Godfraind et al.

(10) Patent No.: US 11,372,182 B2
(45) Date of Patent: Jun. 28, 2022

(54) OPTICAL FIBRES CONNECTOR FOR OPTOELECTRONIC ACTIVE IMPLANTABLE MEDICAL DEVICE (AIMD)

(71) Applicant: Synergia Medical, Mont-Saint-Guibert (BE)

(72) Inventors: Carmen Godfraind, Mont-Saint-Guibert (BE); Pascal Doguet, Mont-Saint-Guibert (BE); Aurélie De Cock De Rameyen, Mont-Saint-Guibert (BE); Aurore Nieuwenhuys, Mont-Saint-Guibert (BE); Vincent Callegari, Mont-Saint-Guibert (BE)

(73) Assignee: SYNERGIA MEDICAL, Mont-Saint-Guibert (BE)

( * ) Notice: Subject to any disclaimer, the term of this patent is extended or adjusted under 35 U.S.C. 154(b) by 0 days.

(21) Appl. No.: 17/271,624

(22) PCT Filed: Aug. 31, 2018

(86) PCT No.: PCT/EP2018/073436
§ 371 (c)(1),
(2) Date: Feb. 26, 2021

(87) PCT Pub. No.: WO2020/043302
PCT Pub. Date: Mar. 5, 2020

(65) Prior Publication Data
US 2021/0318502 A1  Oct. 14, 2021

(51) Int. Cl.
*H04B 10/00* (2013.01)
*G02B 6/42* (2006.01)
(Continued)

(52) U.S. Cl.
CPC ......... *G02B 6/4292* (2013.01); *A61N 5/0622* (2013.01); *G02B 6/4248* (2013.01); *G02B 6/43* (2013.01); *A61N 2005/063* (2013.01)

(58) Field of Classification Search
CPC combination set(s) only.
See application file for complete search history.

(56) References Cited

U.S. PATENT DOCUMENTS 4,060,309 A * 11/1977 Le Noane ............ G02B 6/3843
385/33
4,279,469 A * 7/1981 Forman ................. G02B 6/406
385/60
(Continued)

FOREIGN PATENT DOCUMENTS

EP       0081192 A1   6/1983
WO    2006111160 A1   10/2006
(Continued)

OTHER PUBLICATIONS

Int'l Search Report for PCT/EP2018/073436, dated May 15, 2019.

*Primary Examiner* — Agustin Bello
(74) *Attorney, Agent, or Firm* — Blue Filament Law PLLC

(57) ABSTRACT

An optical fibres connector for an optoelectronic active implantable medical device (AIMD) for implantation in a living body is provided. The optical fibres connector includes a male component (M) coupled to a first set of optical fibres, a female component (F) coupled to a second set of optical fibres or optical elements, and a coupling component (C) for reversibly locking the male and female components in a coupled position. The optical fibres or optical elements are in perfect alignment. The coupling component includes a fixed element (40*f*) and a rotatable element (40*r*) all optical fibres (41*f*) and optical elements of the connector remaining static upon rotation of the rotatable (Continued)

element, reversibly locking the male and female components in the coupled position is achieved by rotating the rotatable element with respect to the fixed element.

13 Claims, 8 Drawing Sheets

(51) Int. Cl.
*A61N 5/06* (2006.01)
*G02B 6/43* (2006.01)

(56) References Cited

U.S. PATENT DOCUMENTS

| | | | | |
|---|---|---|---|---|
| 4,285,572 A * | 8/1981 | Beaudette | ............ | G02B 6/4292 250/552 |
| 4,494,823 A * | 1/1985 | Yoshida | ............ | G02B 6/4246 385/73 |
| 4,634,214 A * | 1/1987 | Cannon, Jr | ......... | G02B 6/3865 385/86 |
| 4,896,939 A * | 1/1990 | O'Brien | ............ | G02B 6/4448 439/208 |
| 4,991,929 A * | 2/1991 | Bowen | ............ | G02B 6/3887 385/56 |
| 5,267,342 A * | 11/1993 | Takahashi | ............ | G02B 6/3846 385/140 |
| 5,297,227 A * | 3/1994 | Brown | ............ | G02B 6/3897 385/139 |
| 5,574,815 A * | 11/1996 | Kneeland | ............ | H01B 11/1891 174/750 |
| 6,250,818 B1 * | 6/2001 | Loughlin | ............ | G02B 6/266 385/86 |
| 6,351,593 B1 * | 2/2002 | Pollack | ............ | G02B 6/3849 385/59 |
| 6,695,772 B1 * | 2/2004 | Bon | ............ | A61B 17/3421 600/125 |
| 6,974,262 B1 * | 12/2005 | Rickenbach | ......... | G02B 6/3817 385/88 |
| 7,195,505 B1 * | 3/2007 | Becker | ............ | H01R 13/5219 439/282 |
| 7,273,478 B2 * | 9/2007 | Appling | ............ | A61B 18/24 606/7 |
| 8,480,312 B2 * | 7/2013 | Smith | ............ | G02B 6/3817 385/94 |
| 9,004,442 B2 * | 4/2015 | Norris | ............ | F16C 1/108 248/636 |
| 9,057,847 B2 * | 6/2015 | Lin | ............ | G02B 6/387 |
| 9,465,173 B2 * | 10/2016 | Becker | ............ | H01R 13/5219 |
| 9,500,812 B2 * | 11/2016 | Tanaka | ............ | G02B 6/3817 |
| 9,696,500 B2 * | 7/2017 | Barnette, Jr | ............ | G02B 6/389 |
| 9,827,438 B2 * | 11/2017 | Johnson | ............ | G02B 6/3851 |
| 10,082,632 B2 * | 9/2018 | Altshuler | ............ | G02B 6/4206 |
| 10,139,567 B1 * | 11/2018 | Beranek | ............ | G02B 6/3821 |
| 10,413,747 B2 * | 9/2019 | Nielsen | ............ | A61N 1/05 |
| 10,663,677 B2 * | 5/2020 | Altshuler | ............ | G02B 6/3861 |
| 10,688,313 B2 * | 6/2020 | Rogers | ............ | A61N 5/0601 |
| 2004/0010248 A1 * | 1/2004 | Appling | ............ | A61B 18/24 606/15 |
| 2015/0012072 A1 * | 1/2015 | Johnson | ............ | A61N 5/0601 607/92 |
| 2015/0018753 A1 * | 1/2015 | Johnson | ............ | A61N 5/0624 604/21 |
| 2015/0374207 A1 * | 12/2015 | Fukuoka | ............ | G02B 23/2446 600/110 |
| 2017/0285276 A1 * | 10/2017 | Altshuler | ............ | G02B 6/4206 |
| 2018/0078781 A1 * | 3/2018 | Johnson | ............ | A61N 5/0601 |
| 2019/0101709 A1 * | 4/2019 | Wang | ............ | G02B 6/3877 |
| 2020/0386955 A1 * | 12/2020 | Hu | ............ | G02B 6/3894 |
| 2021/0048586 A1 * | 2/2021 | Altshuler | ............ | G02B 6/3897 |
| 2021/0157064 A1 * | 5/2021 | Gaal | ............ | G02B 6/4206 |
| 2021/0318502 A1 * | 10/2021 | Godfraind | ............ | G02B 6/43 |
| 2022/0035102 A1 * | 2/2022 | Zhu | ............ | G02B 6/389 |

FOREIGN PATENT DOCUMENTS

| | | |
|---|---|---|
| WO | 2006121407 A1 | 11/2006 |
| WO | 2015003159 A1 | 1/2015 |
| WO | 2015164571 A2 | 10/2015 |
| WO | 2017173419 A1 | 10/2017 |

* cited by examiner

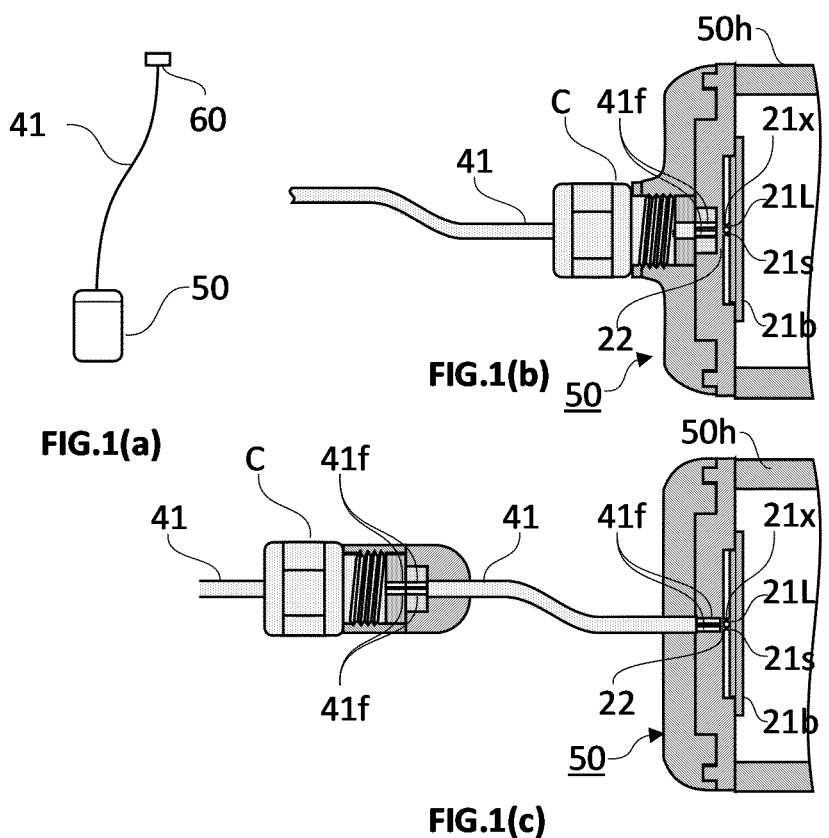
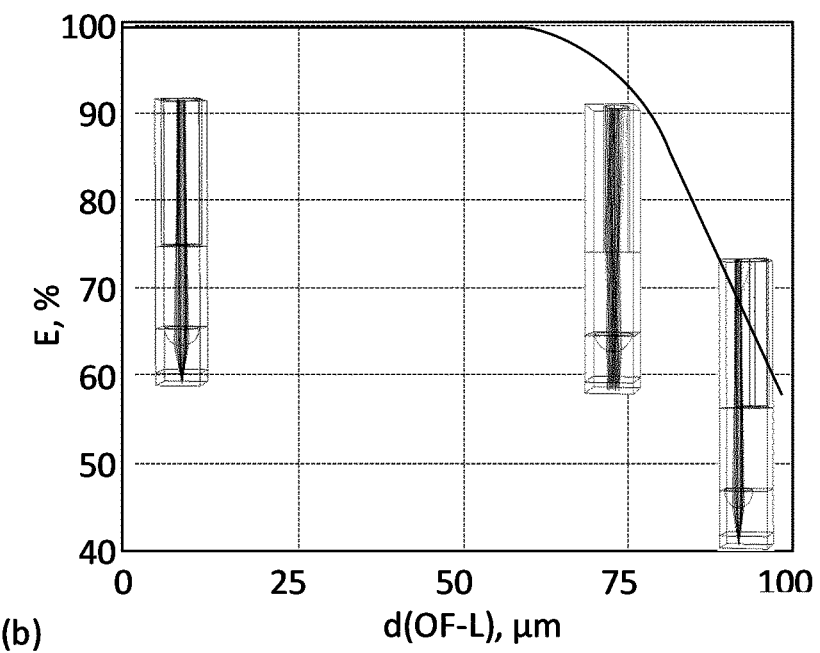
FIG.2

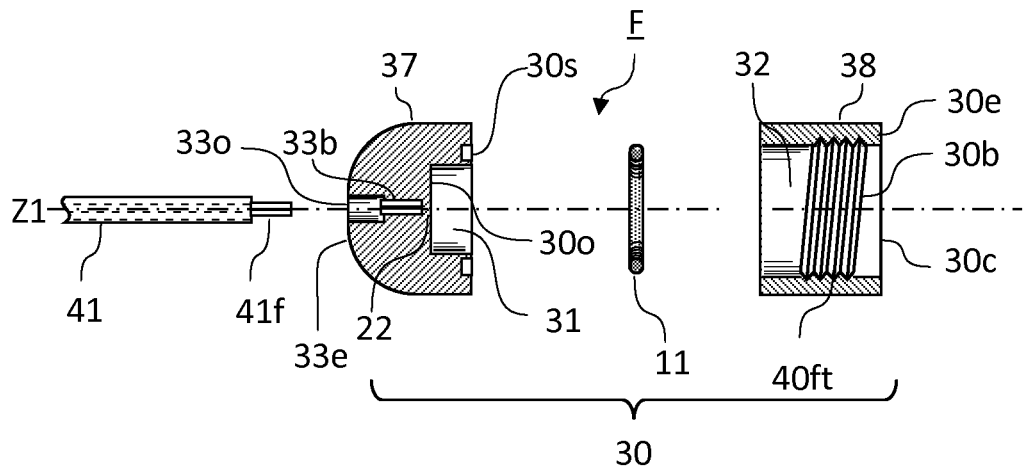
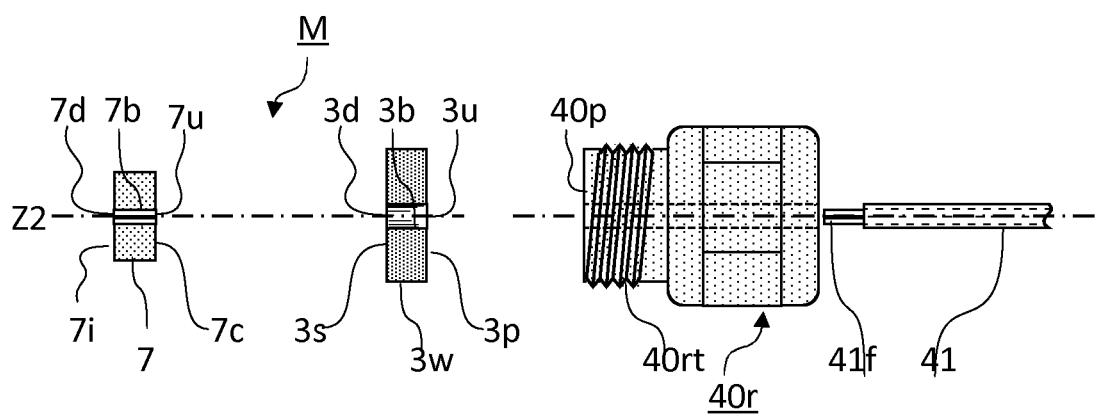
FIG.3(a)
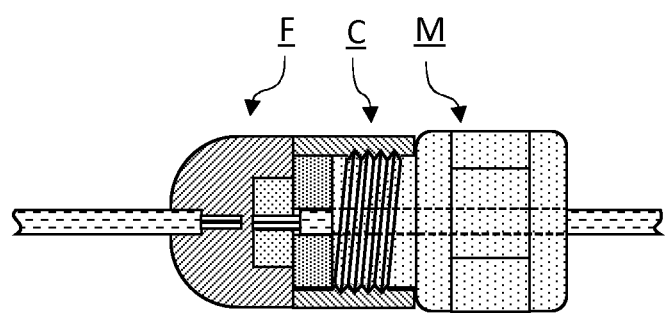
FIG.3(b)

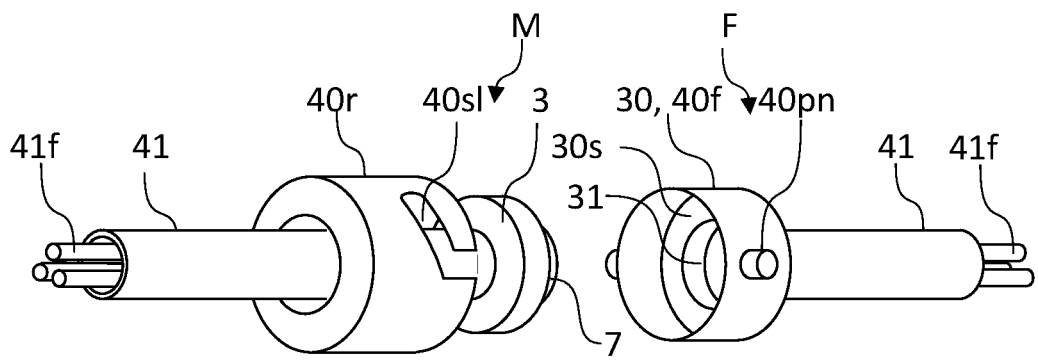
FIG.5
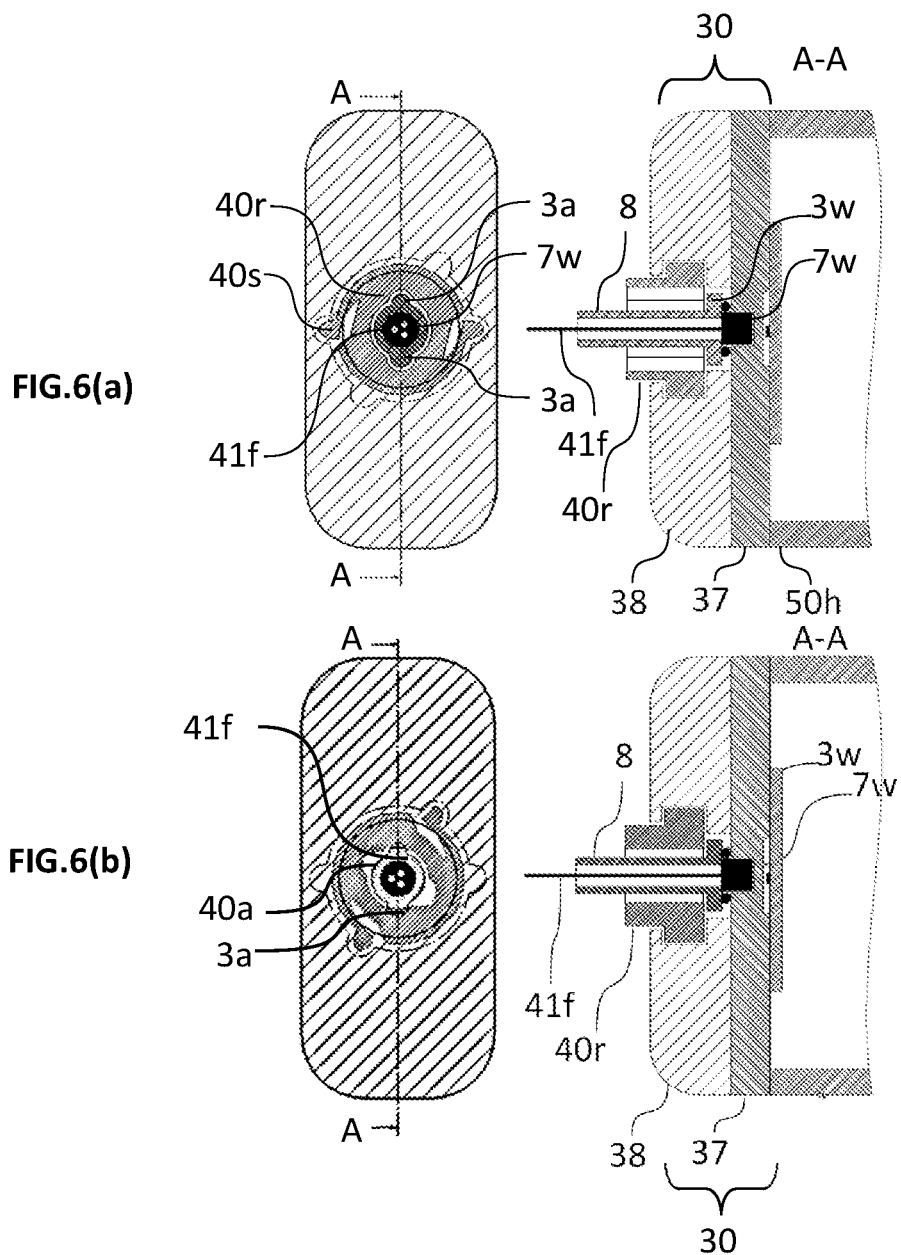
FIG.6(a)
FIG.6(b)

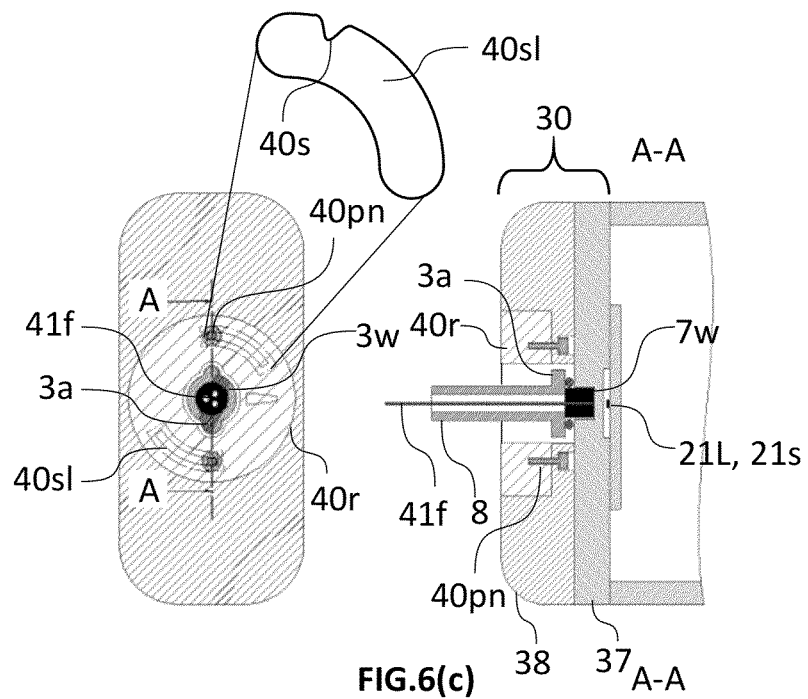
FIG.6(c)
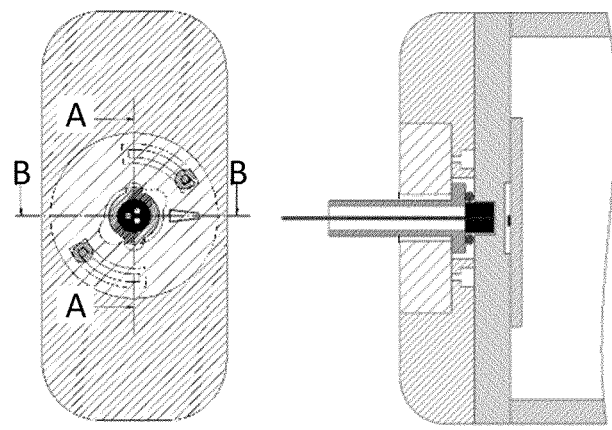
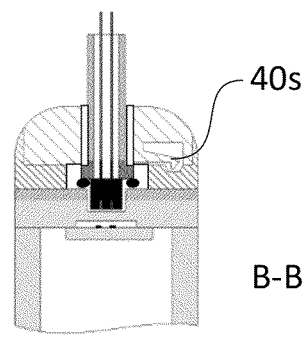
FIG.6(d)

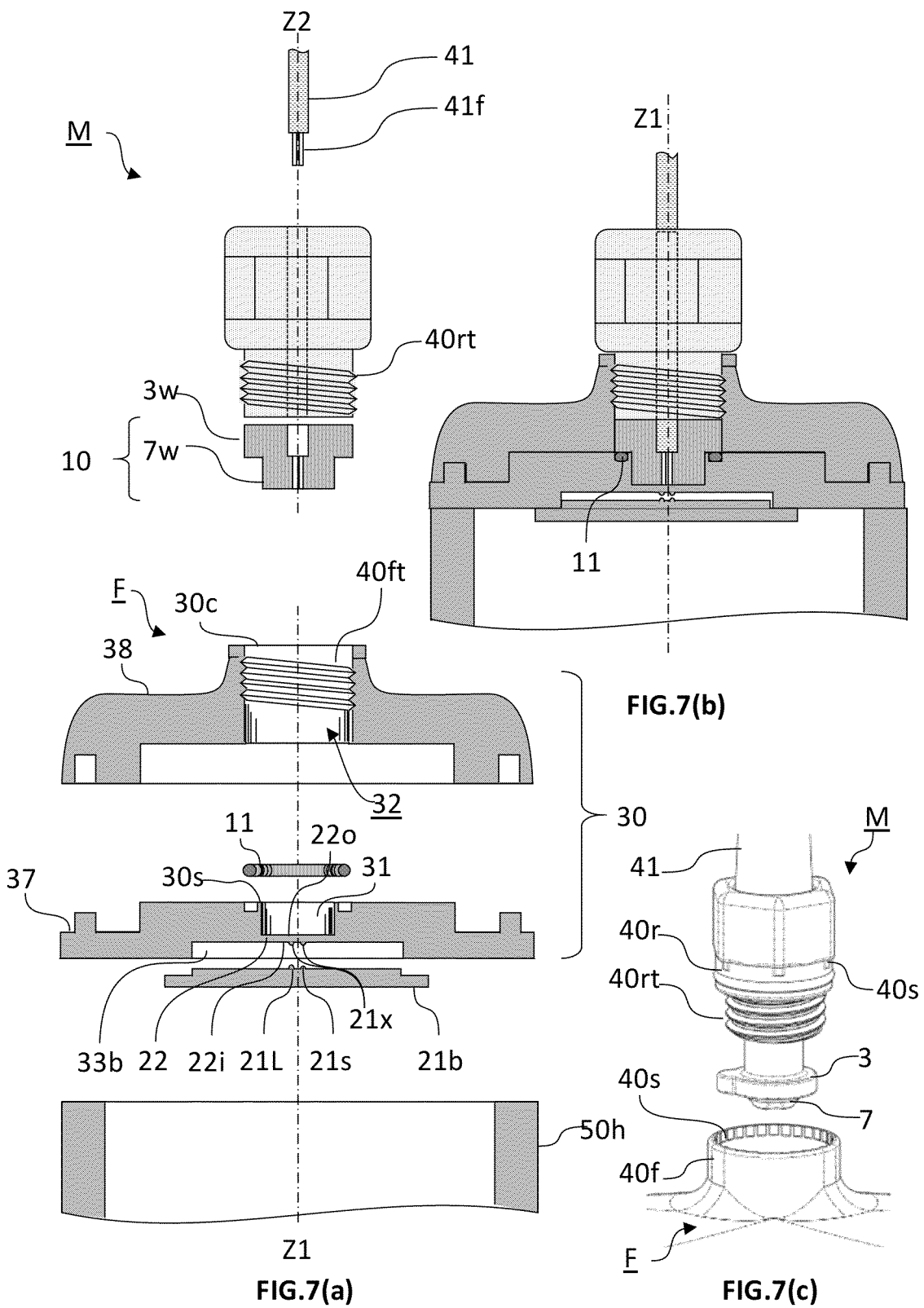

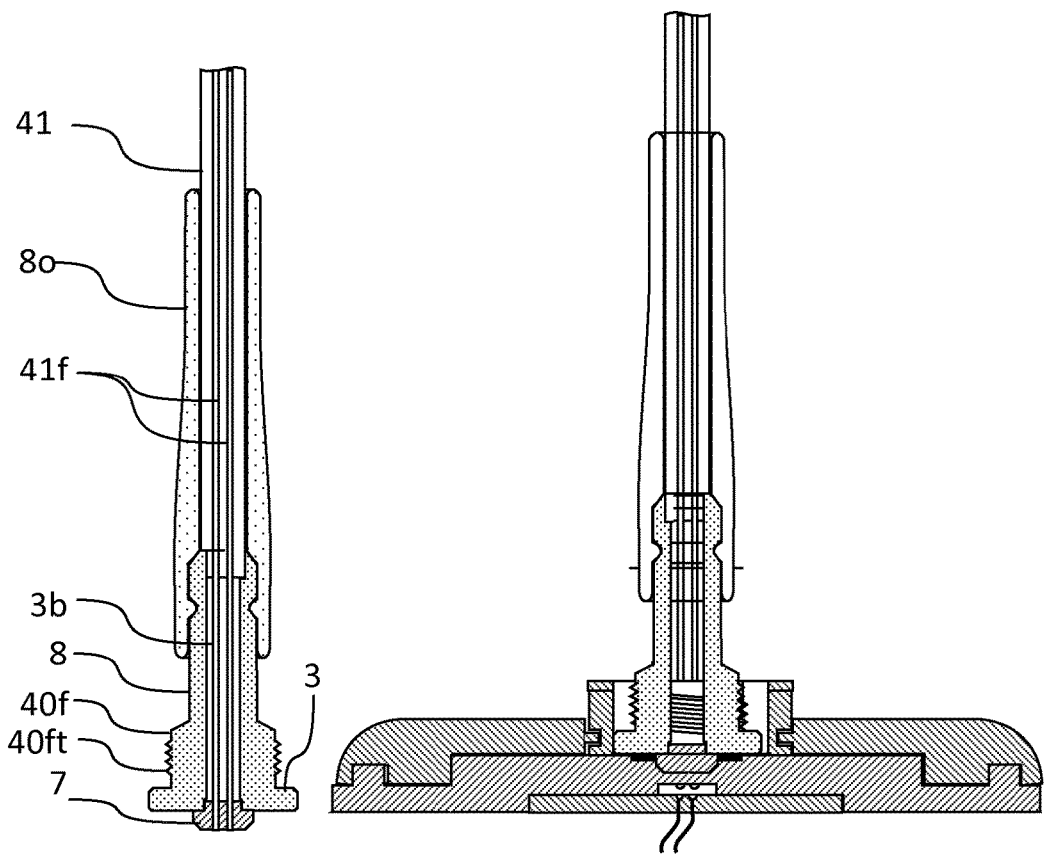
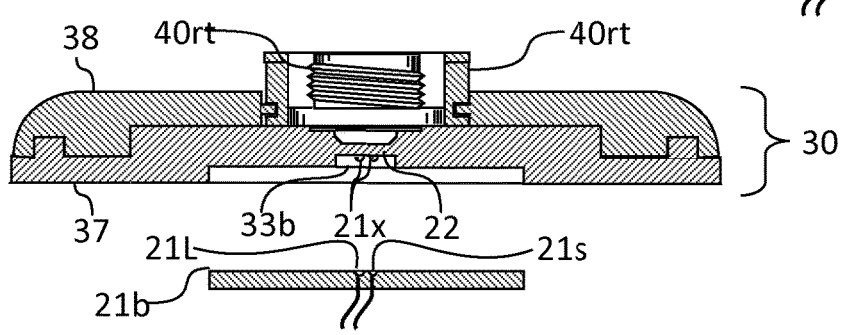
FIG.8(a)
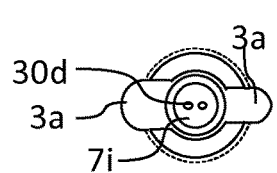
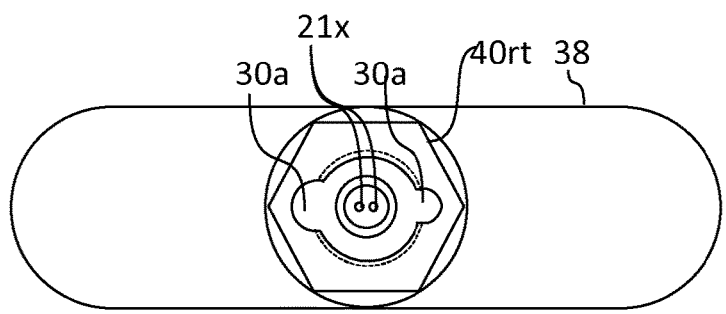
FIG.8(c)   FIG.8(d)

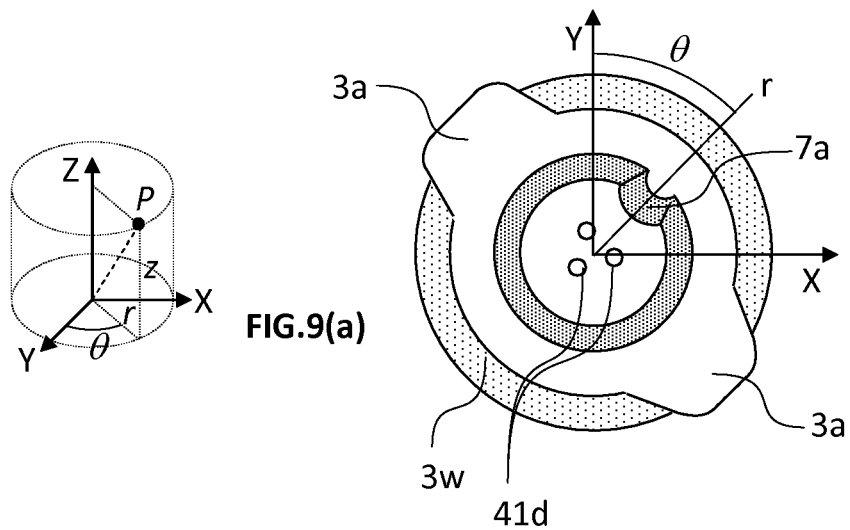
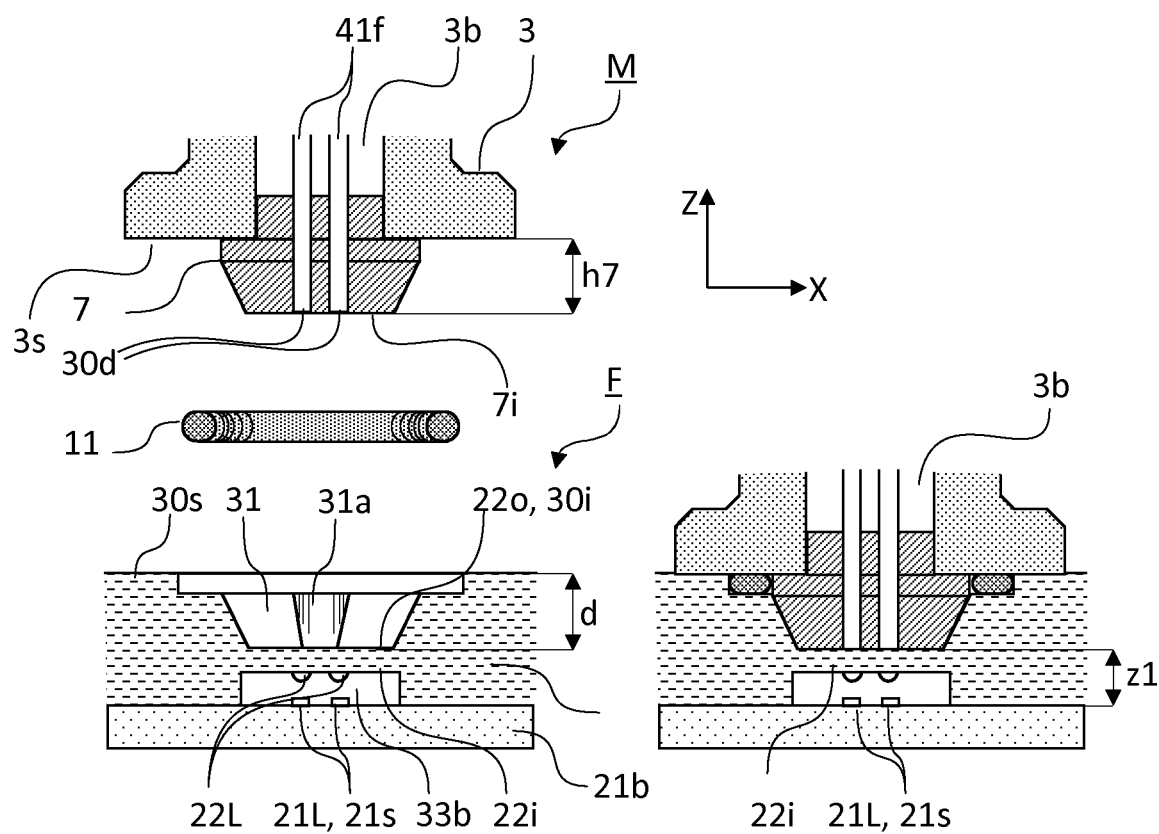
FIG.9(a)
FIG.9(b)     FIG.9(c)

OPTICAL FIBRES CONNECTOR FOR OPTOELECTRONIC ACTIVE IMPLANTABLE MEDICAL DEVICE (AIMD)

TECHNICAL FIELD

The present invention is in the field of active implantable medical devices (AIMD) for use in medical treatments involving the transmission of electrical pulses or light pulses between an energy pulse generator enclosed in an encapsulation unit and a biological tissue by transmission of light energy through optical fibres between the encapsulation unit and the biological tissue. In particular, it concerns a novel concept of connection between a first optical fibre and a second optical fibre or an optical element which can be a light source and/or or light sensor enclosed in an encapsulation unit. The connection of the present invention allows a reproducible, secure, and reversible coupling of the first optical fibre to the second optical fibre or optical element, ensuring an optimal alignment between the optical fibre and the second optical fibre or optical element. The coupling is made easier for the surgeon without losing in alignment accuracy. These advantages can be achieved in a very reproducible manner and without increasing the production costs of the optoelectronic AIMD compared with state of the AIMD's.

BACKGROUND OF THE INVENTION

Active implantable medical devices (AIMD) have been used for decades for treating a number of disorders, in particular neurological disorders. A major type of AIMD's consists of neurostimulators, which deliver electrical pulses to a tissue such as a nerve or a muscle for diagnosing or treating a number of disorders such as Parkinson's disease, epilepsy, chronic pain, motor disorders, and many other applications. Depending on the tissue to be treated, the type of electrodes used, and the distance between electrodes, the voltage required between implanted electrodes is generally of the order of 15V±5V. Such voltage requires an electrical pulse generator of such dimensions that electric stimulating implants are generally formed of two separate components: on the one hand, the electrodes which are implanted directly onto the tissue to be treated and, on the other hand, the electrical pulse generator, of larger dimensions, and encapsulated in a housing, which can be implanted at various locations in the body depending upon the application but most often in the subclavian region, the lower abdominal area or gluteal region. The wires connecting the pulses generator to the electrodes are generally coiled to provide flexibility, to permit the distance from the electrical pulse generator and the electrodes to be varied and to enhance mechanical stability with a higher compliance with respect to body movements. Because of the use of electric wires, in particular when coiled, such implants are incompatible with magnetic resonance imaging (MRI) apparatuses and also with simple metal detecting portals as used in airports, banks, and the like.

In its simplest form, a device for delivering electrical pulses comprises an energy pulse generator lodged in a housing, stimulating electrode contacts, and leads coupling the electrode contacts to the energy pulse generator to transmit energy from the energy pulse generator to the electrode in the form of electrical energy. The energy pulse generator can generate electrical pulses transmitted to the electrode contacts by conductive leads. Alternatively, and as described, e.g., in EP3113838B1, the energy pulse generator can generate light transmitted through optical fibres to photovoltaic cells which transform the light energy into electrical energy which is fed to the electrode contacts. The term "lead" is herein used to define both electric conductors (e.g., wires, tapes) and optical fibres.

In recent years, treatment of tissues with optical energy has shown encouraging potential for the treatment of disorders, either to support the field of optogenetics or using direct infrared light. For such light treatments of a tissue, a so-called optrode can be used. An optrode can be a light emitter focusing a light beam onto a precise area of a tissue, or it can be a light sensor, sensing a reflected, transmitted, or scattered light beam emitted by a light emitter. The light emitter can be powered by electric current in a similar way as the electrodes discussed supra.

As illustrated in FIG. 1, the present invention concerns AIMD's comprising:
- an encapsulation unit (50) including a housing (50h) enclosing a source of energy, any analogue and/or digital circuit, such as a pulse generator, and a source of light emission (21L) and/or a light sensor (21s),
- an electrode unit (60) comprising one or more electrodes and/or optrodes suitable for being implanted directly onto a tissue to be treated, and
- an optical unit (41) comprising one or more optical fibres (41f) for transferring optical energy between the encapsulation unit and the electrode unit.

In continuation such AIMD's are referred to as "optoelectronic AIMD's."

The implantation of an optoelectronic AIMD includes the following steps. A surgeon opens the area comprising the tissue to be treated and couples the electrode unit to said tissue. The electrode unit is generally optically coupled to the distal ends of one or more optical fibres before implanting the electrode unit to the tissue to be treated. Coupling of optical fibres to an electrode unit is described e.g., in PCT/EP2017/071858 [=T0150]

Proximal ends of the one or more optical fibres (opposite the distal end) are then subcutaneously led through a specific guide to the area of implantation of the encapsulation unit, which is dimensionally substantially larger than the electrode unit and is therefore implanted in more appropriate parts of the body. At this stage, the surgeon must implant the encapsulation unit and couple it to the proximal ends of the optical fibres (in any sequence). The latter operation is quite delicate, because the alignment of the optical fibres with any optical elements enclosed in the encapsulation unit must be optimized, lest the transfer of light energy would be insufficient, with substantial energy losses due to misalignments.

FIG. 2 shows the coupling efficiency in % plotted as a function of the misalignment of a lens with an optical fibre. Lenses can be used for optimizing the light beam exiting an optical fibre by, e.g., focusing, orienting, diffracting the light beam, and the like. It can be seen that a misalignment of as little as 50 µm of an optical fibre with a lens yields a brutal drop of the light transfer efficacy between an optical fibre (41f) and the interior of an AIMD's encapsulation unit (50). Considering that the AIMD's must be miniaturized, thus reducing the size of batteries, and that reloading batteries is a cumbersome operation, it is clear that the coupling efficacy between an optical fibre and the interior of an AIMD's encapsulation unit must be optimized. This is only possible with an alignment of the various components of a light coupling unit of within less than 50 µm, preferably less than 30 µm. The issue of (mis-)alignment is even more critical in case more than one optical fibre must be coupled to the encapsulation unit, or simply if at least one optical fibre is offset with respect to any axis of symmetry of the AIMD.

Examples of coupling systems between an encapsulation unit and optical fibres ensuring optimal alignment are described in WO2018068807 [=T0120]. The coupling system described therein, however, comprises loose parts, including a washer and loose screws of small dimensions which can fall off at any time during the coupling operation by the surgeon. Furthermore, the washer is elongated and has dimensions ill-fitted for transfer through a guide from the tissue to be treated to the implantation location of the encapsulation unit.

As illustrated in FIG. 1(c), encapsulation units can be produced and supplied to a surgeon, with sections of limited lengths of one or more optical fibres pre-coupled to the encapsulation unit. This can have the advantages that, on the one hand, the alignment between the optical fibres and the various optical elements enclosed in the encapsulation unit (including sources of light emission, light sensors, or lenses) can be optimized in-plant and, on the other hand, handling by the surgeon of a flexible cable for coupling to the fibre optics coupled to the electrode units can be more comfortable. With such configurations, a connection between the optical fibres coupled to the electrode unit with the optical fibres coupled to the encapsulation unit is required, with the same constraints of optimized two-by-two alignments of the two sets of optical fibres, and of limited dimensions suitable for guiding through a guide. Such optical fibre-to-optical fibre connectors are, to our knowledge, not available to date on the market in the field of AIMD's.

The present invention proposes an optoelectronic AIMD comprising an optical fibre connector allowing the connection of a first set of one or more optical fibres to an encapsulation unit containing optical elements or to a second set of one or more optical fibres. The connection allows optimal alignment of the first set of one or more optical fibres with the optical elements or with the one or more optical fibres of the second set, in a user-friendly manner, required in the stressful conditions and confined space of a surgical operation. Furthermore, the connector of the present invention can easily be designed without any metal parts which are problematic for magnetic resonance imaging (MRI), anti-metal security portals, and the like. These and other advantages are described in more details in the following sections.

SUMMARY OF THE INVENTION

The present invention is defined in the appended independent claims. Preferred embodiments are defined in the dependent claims. In particular, the present invention concerns an optical fibres connector for an optoelectronic active implantable medical device (AIMD) for implantation in a living body. An active implantable medical device is a medical device which can be implanted in a patient's body and which is suitable for activating a function interacting with the patient's body. This is by opposition to a passive implantable medical device, such as a stent, which cannot be activated after implantation. The present optical fibres connector comprise a female component, a male component, and a coupling component.

The female component comprises a female support element and one or more optical elements. The female support element comprising a support locking end and a support optics end, and is provided with, a coupling bore portion extending along a first longitudinal axis, Z1, between a bore locking end and a bore optics end (30o), said coupling bore portion comprising
    a receiving portion opening at the support locking end and forming at an opposite end a shoulder surrounding,
    a cavity adjacent to the receiving portion of given depth, d, measured along the first longitudinal axis, Z1, and ending at the bore optics end forming a female interface surface, and
at least one optics bore portion extending parallel to the first longitudinal axis, Z1, from an optics bore end opening at the support optics end, and either,
    to an opening at the female interface surface, thus defining at least one female through-bore extending from the support optics end to the support locking end, or
    to an inner surface (22i) of a window (22) separated from the cavity by a thickness of the window (22) comprising an outer surface (22o), wherein said window is transparent to selected light wavelengths range.

The one or more optical elements are selected from,
at least one optical fibre comprising an optical fibre proximal end, and being inserted in the corresponding at least one optics bore portion, such that the optical fibre proximal end is at a predefined distance from the female interface surface of the cavity, and is preferably flush with said female interface surface or is preferably in contact with the inner surface of the window, or
at least one source of light emission and/or light sensor, facing the inner surface of the window.

The male component comprises a male support element comprising a washer portion, a male tip, and an optical fibre. The washer portion comprises at least one male through-bore extending parallel to a second longitudinal axis, Z2, from a washer inlet opening at a back surface to a washer outlet opening at a support surface of the washer portion. It has a geometry allowing insertion thereof into the coupling bore portion of the female support element until the support surface contacts the shoulder of the female component.

The male tip is coupled to the support surface of the washer portion, and comprises,
    a male interface surface having a geometry mating the cavity geometry, such that the male tip snugly fits in the cavity,
    one or more male through-bores extending parallel to the second longitudinal axis, Z2, from a tip inlet in fluid communication with the at least one male through-bore to a tip outlet, opening at the male interface surface,
    an optical fibre inserted in each of the one or more male through-bores (7b), and comprising an optical fibre proximal end, which is at a predefined distance from the tip outlet (7d), preferably flush with the tip outlet.

The coupling component is suitable for reversibly locking the male and female components in a coupled position. The coupled position is defined by the male component being coaxially inserted in the receiving portion of the female component with the first and second longitudinal axes, Z1 and Z2, being coaxial and with the support surface of the washer resting on the shoulder of the receiving portion, and with the male tip unit being fitted in the cavity,
    with the male interface surface being located at a predefined distance measured along the longitudinal axis, Z2, from the female interface surface, preferably in contact with one another, the proximal ends of the one or more optical fibres of the male element are in perfect alignment with the one or more optical elements of the female component.

The coupling component comprises a fixed element and a rotatable element being rotatable about the first and/or second longitudinal axis, Z1, Z2, with respect to the fixed element. All the optical fibres and optical elements of the connector remain static upon rotation of the rotatable element. Reversibly locking the male and female components in the coupled position is achieved by rotating the rotatable element with respect to the fixed element.

It is important that both female component and male component comprise no loose part, and all elements of the coupling component are attached to the male and/or female components. Finally, for ease of insertion of the male component through a guide, the male component and any element of the coupling component attached thereto have a dimension normal to the second longitudinal axis, Z2, inscribed in a circle having a diameter of not more than 15 mm and preferably of not more than 10 mm, more preferably not more than 7 mm.

In many embodiments, at least one or more optical elements are offset with respect to the first longitudinal axis, Z1. For example, if there are at least two optical elements which are not concentric, at least one is offset with respect to the first longitudinal axis, Z1. For the proximal ends of the one or more optical fibres of the male element to be in perfect alignment with the one or more optical elements of the female component, comprising at least one optical element offset with respect to the first longitudinal axis, Z1, at least one optical fibre inserted in a male through-bore must necessarily be offset with respect to the second longitudinal axis, Z2.

In order to ensure coupling the male and female components with a correct azimuthal angle for the at least one offset optical element to face the at least one optical fibre, the following alternative or concomitant solutions are available.

In one embodiment, the cavity has a cavity cross-section normal to the first longitudinal axis, Z1, defining a non-revolution geometry at least over a portion of the depth of the cavity. The male tip and the male interface surface have a non-revolution geometry with respect to the second longitudinal axis, Z2, mating the non-revolution geometry of the cavity cross-section, such that the male tip fits in the cavity with a finite number of azimuthal angles only, and such that at any of said finite number of azimuthal angles, the one or more optical elements of the female component face the one or more optical fibres inserted in the at least one male through-bore. The alignment of the optical elements with corresponding optical fibre should be within a tolerance of less than ±50 µm, preferably of less than ±30 µm, in order to minimize the energy losses of the light passing through the connector.

In an alternative embodiment or in the same embodiment, the washer portion has a non-revolution geometry with respect to the second longitudinal axis, Z2, mating the non-revolution geometry of the coupling bore cross-section, such that the washer portion fits in the coupling bore portion with said finite number of azimuthal angles only. At any of said finite number of azimuthal angles one or more optical elements of the female component face the optical fibre inserted in the at least one male through-bore (7b), within a tolerance preferably of less than ±100 µm, more preferably of less than ±70 µm, more preferably of less than ±50 µm, and most preferably of less than ±30 µm. If this is an alternative embodiment to the previous embodiment, the tolerance should be in the lower range. If it is combined with the preceding embodiment, the tolerance can be in the higher range, and is useful to pre-orient the male and female components, prior to reaching the coupled position with a tight tolerance obtained between the cavity and the male tip.

With one or with both previous embodiments, if an optical fibres connector has a female component comprising more than one optical element, and a male component comprising more than one male through-bore (7b) supporting an optical fibre, the male and female components can be arranged in the coupled position such that at any of said finite number of azimuthal angles optical fibre faces at least one corresponding optical element, within the tolerance preferably of less than ±50 µm, preferably of less than ±30 µm.

From a construction point of view, the female support element can be monolithic or, alternatively, can comprise multiple components, including
  a coupling unit comprising the receiving portion of the bore, the coupling unit being preferably made of a polymeric material or metal, and
  A female tip unit comprising the cavity and the one or more fibre through-bores or the window, said female tip unit being preferably made of a ceramic material, more preferably a glass material,
Similarly, the male support element can be monolithic or, alternatively, can comprise multiple components, including:
  A washer unit forming the washer portion and
  A male tip unit forming the male tip and comprising a male tip unit coupling portion for coupling to the support surface of the washer portion.

With no joints, monolithic components are advantageous in terms of sealing properties and durability, but the design freedom and ease of manufacturing can be difficult. Multiple components enhance design freedom, facilitates manufacturing, and ease of coupling of the optical fibres and optical elements to the male and female components. Great care must, however, be taken with the seal and durability of the joints.

The male component can comprise a sleeve integral with or coupled to the back surface of the washer portion and comprising at least a sleeve bore coaxial with the at least one male through-bore of the washer portion and forming together at least one single bore extending along the second longitudinal axis, Z2, from a sleeve inlet to the washer outlet. The washer portion forms a flange extending outwardly over a perimeter of the washer outlet.

In one embodiment, the female component can be part of an encapsulation unit. The encapsulation unit can comprise a housing defining an inner space sealed from an outside of the housing, wherein the inner surface of the window belongs to the inner space and the outer surface of the window faces the outside. The at least one optical element is located in the inner space, facing the inner surface of the window. It is preferably mounted on a board supporting the at least one optical element at a predefined distance from the inner surface of the window and at a predefined azimuthal angle about the first longitudinal axis, Z1. In in the coupled position, each optical component must face at least one corresponding male through-bore or each through bore (7b) must faces at least one optical element, within the tolerance, preferably of less than ±20 µm, preferably of less than ±5 µm. The housing also contains in the inner space thereof one or more components selected from a source of electric power, or an analogue and/or digital circuit.

The optical fibres connector preferably comprises at least one sealing element. At least one sealing element can sit on the shoulder of the coupling bore portion and enclose a circumference of the cavity. The sealing element seals the female interface surface of the cavity from an outside environment, when the male and female components are locked in the coupled position.

The coupling component is preferably one of the nut-screw type, the bayonet type, or the key-lock type, with or without a snap-fitting element. A nut-screw type coupling component is defined as follows.

The fixed element of a nut-screw type coupling component comprises a fixed thread centred on the first or second longitudinal axis, Z1, Z2, which is located on the female or the male component, respectively. The rotatable element comprises a nut provided with a rotatable thread mating the fixed thread, and mounted on the male or the female element, respectively. The nut can rotate about and translate along the second or first longitudinal axis, Z2, Z1, respectively. It is important that the nut cannot be removed easily from the male or female component (i.e., without a special tool or a specific manipulation of the nut). The rotatable thread can be engaged into the fixed thread when the male tip is engaged in the cavity, and the rotation of the nut over the fixed thread translates the washer portion along the coaxial first and second longitudinal axes, Z1, Z2, towards the female interface surface, until the support surface of the washer contacts the shoulder of the female component.

A bayonet type coupling component comprises one or more pins extending radially out of one of the fixed or rotatable element, and a corresponding number of L-shaped slots provided on the other of the fixed or rotatable element comprising the one or more pins. Each L-shaped slot comprises a first segment extending from an open end parallel to the first or second longitudinal axis, Z1, Z2, and a second segment extending transverse to the first segment to a closed end, and preferably forming an angle of at least 90° with the first segment. As the male and female components are brought into the coupled position by translation along the coaxial first and second longitudinal axes, Z1, Z2, each pin engages into the first segment of the corresponding L-shaped slot until it reaches the second segment. The male and female components are locked in their coupled position by rotation of the rotatable element, thus running each pin along the second segment of the corresponding L-shaped slot.

A key-lock type coupling component is defined as follows. The washer has a non-revolution geometry and comprises one or more protrusions extending outwards and radially with respect to the second longitudinal axis, Z2. The rotatable element comprises a keyhole opening normal to the first longitudinal axis, Z1, and comprising one or more recesses mating the one or more protrusions of the washer. The washer can be inserted through the keyhole opening with a limited number of azimuthal angles only. As the male and female components are brought into the coupled position by translation along the coaxial first and second longitudinal axes, Z1, Z2, the washer is inserted through the keyhole opening, until the support surface of the washer contacts the shoulder of the female component. The male and female components are locked in their coupled position by rotation of the rotatable element, thus offsetting the one or more recesses with respect to the corresponding one or more protrusions of the washer.

For any of the foregoing coupling components, it is preferred that the rotation of the rotatable element with respect to the fixed element also drives a translation of the male component along the coaxial longitudinal axes, Z1, Z2, towards the female component, until the support surface of the washer contacts the shoulder of the female component. This is necessarily the case with a nut-screw type of coupling components but requires specific features for bayonet and key-lock types of coupling components.

The coupling component preferably comprises a snap-fitting element comprising a resilient lever provided with a protrusion. The rotatable element can rotate with the resilient lever in a biased configuration, until the protrusion reaches a corresponding recess in which it can engage thus releasing the bias and reaching a snapped position. This has the double advantage to indicate to the surgeon that the coupled position has been reached, and it ensures that the rotatable element does not spontaneously rotate to unlock the connector, due to body movements when inserted in a patient.

The present invention also concerns an optoelectronic active implantable medical device (AIMD) for implantation in a living body, comprising an optical fibres connector as defined supra, connecting a first set of one or more optical fibres coupled to an electrode and/or optrode unit either,
  to an encapsulation unit enclosing one or more optical elements, in perfect alignment with the first set of one or more optical fibres, preferably within a tolerance of less than ±50 μm, preferably of less than ±30 μm, or
  to a second set of optical fibres, in perfect two-by-two alignment with the first set of one or more optical fibres, preferably within a tolerance of less than ±50 μm, preferably of less than ±30 μm.

BRIEF DESCRIPTION OF THE FIGURES

For a fuller understanding of the nature of the present invention, reference is made to the following detailed description taken in conjunction with the accompanying drawings in which:

FIG. 1: shows (a) an AIMD according to the present invention, (b) an example according to the present invention of a connection of a first set of optical fibres to an encapsulation unit, and (c) an example according to the present invention of a connection of a first set of optical fibres to a second set of optical fibres.

FIG. 2: shows the coupling efficiency, E (%), of light transmission between a source of light and an optical fibre as a function of a misalignment, d(OF-L) between the optical fibre and a micro-optical lens.

FIG. 3: shows an example of connector according to the present invention, with the rotatable element of the coupling component located on the male component (a) in exploded view, and (b), in the coupled position.

FIG. 5: shows a coupling component of a bayonet type.

FIG. 6: shows two embodiments of a coupling component of a key-lock type: (a) & (b) including snap-fitting devices (a) in open and (b) locked positions, and (c) & (d) including guiding pins inserted in bean-shaped slots (c) in open and (d) locked positions.

FIG. 7: shows an embodiment of connector according to the present invention between optical fibres and an encapsulation unit, comprising a rotatable element provided with a rotatable thread and mounted on the male component, (a) exploded view, (b) assembled view, (c) provided with snap-fitting elements.

FIG. 8: shows an embodiment of connector according to the present invention between optical fibres and an encapsulation unit, comprising a rotatable element provided with a rotatable thread and mounted on the encapsulation unit forming the female component, (a) exploded view, (b) assembled view, (c) front view of the male component, and (d) front view of the female component.

FIG. 9: shows an embodiment of male tip unit and mating cavity having a non-revolution geometry, allowing for a coupling with a single azimuthal angle.

DETAILED DESCRIPTION OF THE INVENTION

AIMD

Figure 4A:
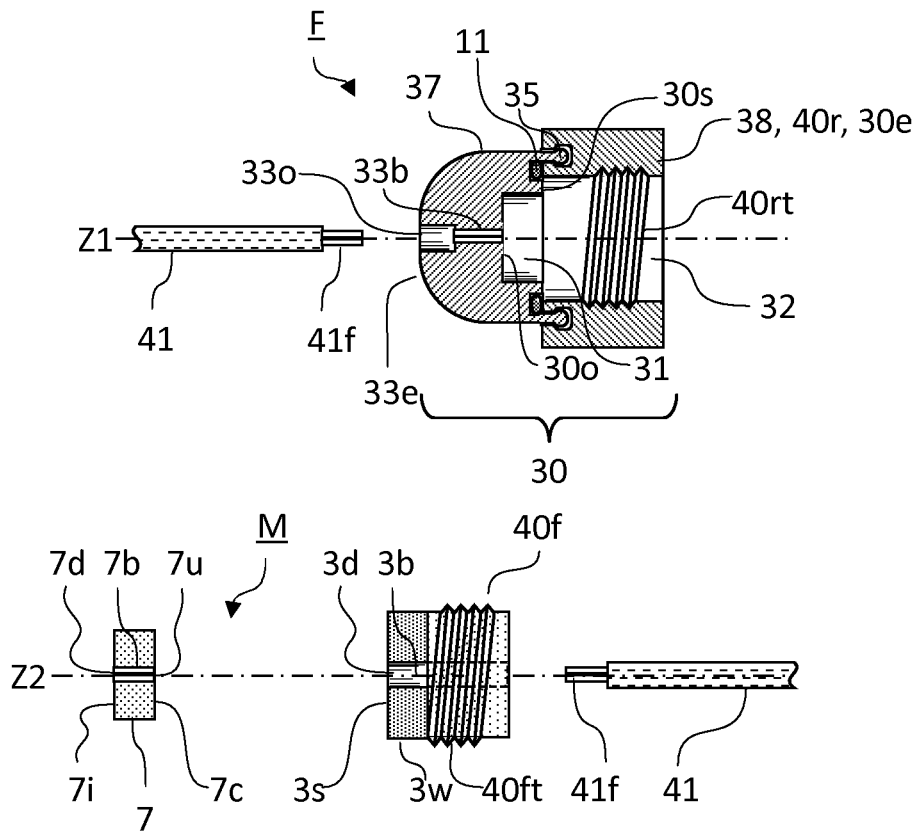
FIG. 4: shows an example of connector according to the present invention, with the rotatable element of the coupling component located on the female component (a) in exploded view, and (b), in the coupled position.

As illustrated in FIG. 1(a), the present invention concerns optoelectronic active implantable medical devices (AIMD) comprising an encapsulation unit (50), an electrode unit (60) comprising electrodes and/or optrodes, and an optical unit (41) comprising one or more optical fibres (41*f*).

The encapsulation unit (50) is formed by a housing (50*h*) defining an inner space enclosing one or more optical components including one or more sources of light emission, light sensors, micro-optics components (e.g., lenses), an electronic unit (e.g., an analogue and/or digital circuit) for controlling the one or more sources of light emission and/or for processing any information received from a light sensor, and a source of power for powering the at least one source of light emission and the electronic unit. An example of encapsulation unit suitable for the present invention is described in WO2018068807 [=T0120].

The electrode unit (60) typically comprises at least a pair of electrodes having a geometry suitable for contacting a tissue to be treated. If the tissue to be treated is a nerve, the electrodes can be in the form of a cuff electrode comprising a support which can be rolled around the nerve to be treated with the electrodes contacting said nerve. Examples of cuff electrodes suitable for the present invention are described in PCT/EP2017/081408 [=T0200]. Other geometries are adapted for treatments of other tissues, and are well known in the art. The present invention is not restricted to any of geometries of the electrode unit. Because in optoelectronic AIMD's, energy is supplied from the encapsulation unit (50) to the electrode unit (60) in the form of light energy, an electrode unit comprising electrodes is also provided with a photovoltaic cell to transform light energy into electrical energy to feed the electrodes with an electrical current.

For light treatment of a tissue, a so-called optrode can be used. An optrode can be a light emitter focusing a light beam onto a precise area of a tissue, or it can be a light sensor, sensing a reflected, transmitted, or scattered light beam emitted by a light emitter. A light emitter can be in the form of a bevelled edge optical fibre or of an optical fibre coupled to a lens, focusing a light beam on a precise area of a tissue to be treated. Alternatively, the light emitter can be one or more light emitting sources, such as a light emitting diode (LED), a vertical-cavity surface-emitting laser (VCSEL), or another type of laser diode. The light emitting source can be powered by electric current in a similar way to the electrodes discussed supra.

Light energy is transferred between the encapsulation unit (50) and the electrode unit (60) by one or more optical fibres (41*f*) forming an optical unit (41) usually wrapped in a common sheath.

Because the encapsulation unit (50) and electrode unit (60) are implanted separately, with the optical unit generally pre-attached to the electrode unit, an optical connection between the encapsulation unit and electrode unit must be established by a surgeon after at least the electrode unit was implanted and, often, after the encapsulation unit was implanted, or at least partially implanted. The present invention proposes a novel optical fibres connector for optically connecting an encapsulation unit to an electrode unit. In particular, the optical fibre connector permits an easy, accurate, and reproducible connection between a first set of one or more optical fibres (41*f*) of an optic unit (41) either to a set of one or more optical elements including sources of light emission, light sensors, optical components (cf. FIG. 1(b)), or to a second set of one or more optical fibres (41*f*) coupled to the encapsulation unit (cf. FIG. 1(c)).

The optical fibres connector of the present invention comprises a female component (F), a male component (M), and a coupling component (C) for locking the male and female components in the coupled position.

The Female Component (F)

As shown in FIGS. 3(a) and 4(a) the female component (F) comprises:
(a) a female support element (30) comprising a support locking end (30*e*) and a support optics end (33*e*), said female support element being provided with,
    a coupling bore portion (30*b*) extending along a first longitudinal axis, Z1, between a bore locking end (30*c*) and a bore optics end (30*o*), said coupling bore portion comprising
        a receiving portion (32) opening at the support locking end and forming at an opposite end a shoulder (30*s*) surrounding,
        a cavity (31) adjacent to the receiving portion of given depth, d, measured along the first longitudinal axis, Z1, and ending at the bore optics end forming a female interface surface, and
    at least one optics bore portion (33*b*) extending parallel to the first longitudinal axis, Z1, from an optics bore end (33*o*) opening at the support optics end, and either,
        to an opening at the female interface surface, thus defining at least one female through-bore extending from the support optics end to the support locking end, or
        to an inner surface (22*i*) of a window (22) separated from the cavity by a thickness of the window (22) comprising an outer surface (22*o*), wherein said window is transparent to a selected light wavelengths range,
(b) one or more optical elements selected from,
    at least one optical fibre (41*f*) comprising an optical fibre proximal end (41*p*), and being inserted in the corresponding at least one optics bore portion (33*b*), such that the optical fibre proximal end is at a predefined distance from the female interface surface of the cavity, and is preferably flush with said female interface surface or preferably in contact with the inner surface of the window,
    at least one source of light emission (21L) and/or light sensor (21*s*), facing the inner surface (22*i*) of the window (22).

The female support element can be monolithic. Alternatively, as shown in FIGS. 3(a), 6 to 8, and 9(b), the female support element can comprise multiple components, including
    A coupling unit (38) comprising the receiving portion of the bore; the coupling unit is preferably made of a polymeric material or of metal, and
    A female tip unit (37) comprising the cavity and the one or more fibre through-bores (33*b*) or the window (22), said female tip unit being preferably made of a ceramic material, more preferably a glass material, allowing great design accuracy, the dimensions thereof remaining stable with time and temperature variations.

In a preferred embodiment illustrated in FIGS. 1(*b*), 6 to 8, the female component (F) is part of an encapsulation unit, wherein The encapsulation unit comprises a housing (50*h*) defining an inner space sealed from an outside of the housing, wherein the inner surface (22*i*) of the window (22) belongs to the inner space and the outer surface (22*o*) of the window faces the outside, The at least one optical component including at least one source of light emission and/or at least one light sensor is located in the inner space, facing the inner surface of the window. It is preferably mounted on a board (21*b*) supporting the at least one source of light emission and/or light sensor at a predefined distance from the inner surface of the window and at a predefined azimuthal angle about the first longitudinal axis, Z1.

One or more components selected from a source of electric power, or an analogue and/or digital circuit, are contained in the inner space.

The Male Component (M)

The male component (M) comprises a male support element (10) comprising:
(a) a washer portion (3*w*) comprising at least one male through-bore (3*b*) extending parallel to the second longitudinal axis, Z2, from a washer inlet (3*u*) opening at a back surface (3*p*) to a washer outlet (3*d*) opening at a support surface (3*s*) of the washer portion, said washer portion having a geometry allowing insertion thereof into the coupling bore portion (30*b*) of the female support element until the surface portion contacts the shoulder (30*s*) of the female component,
(b) a male tip (7*w*) coupled to the support surface of the washer portion, and comprising,
a male interface surface (7*i*) having a geometry mating the cavity geometry, such that the male tip snugly fits in the cavity,
at least one male through-bore (7*b*) extending parallel to the second longitudinal axis, Z2, from a tip inlet (7*u*) in fluid communication with the at least one male through-bore (3*b*) to a tip outlet (7*d*), opening at the male interface surface (7*i*),
at least one optical fibre (41*f*) inserted in the at least one male through-bore (7*b*) and comprising an optical fibre proximal end (41*p*), which is at a predefined distance from the tip outlet (7*d*), preferably flush with the tip outlet.

The male support element (10) can be monolithic, as shown in FIG. 7(*a*). Alternatively, as shown in FIGS. 3(*a*) and 4(*a*), the male support element can comprise multiple components, including:

A washer unit (3) forming the washer portion (3*w*) and

A male tip unit (7) forming the male tip (7*w*) and comprising a male tip unit coupling portion (7*c*) for coupling to the support surface (3*s*) of the washer portion.

As shown in FIGS. 6 & 8, the male component (M) can comprise a sleeve (8) integral with or coupled to the back surface of the washer portion (3*w*) and comprising at least a sleeve bore coaxial with the at least one male through-bore (3*b*) of the washer portion and forming together at least one single bore extending along the second longitudinal axis, Z2, from a sleeve inlet to the washer outlet (3*d*), and wherein the washer portion (3*w*) forms a flange extending outwardly over a perimeter of the washer outlet (3*d*). The sleeve prevents sharp kinks or fractures to form in the optical unit at the level of the optical fibres connector, where stresses can be concentrated. As shown in FIG. 8, a protective sheath (8*o*); which is flexible can be used to further protect the optical fibres from breaking or from bending too sharply.

Coupled Position of the Male and Female Components

The male and female components can be assembled into a coupled position, wherein the coupled position is defined by the male component being coaxially inserted in the receiving portion of the female component with the first and second longitudinal axes, Z1 and Z2, being coaxial and with the support surface (3*s*) of the washer resting on the shoulder (30*s*) of the receiving portion, and with the male tip unit being fitted in the cavity, with the male interface surface (7*i*) being located at a predefined distance, measured along the longitudinal axis, Z2, from the female interface surface (30*i*), preferably in contact with one another, the proximal ends of the one or more optical fibres of the male element are in perfect alignment with the one or more optical components of the female element. The expression "perfect alignment" is used herein as synonym of "optimal alignment", which is defined as an alignment within a tolerance of preferably less than ±50 µm, preferably less than ±30 µm.

The support surface (3*s*) of the washer resting on the shoulder (30*s*) to define the predefined distance between male and female interface surfaces, is particularly advantageous when (a) when a non-zero distance is desired between the male and female interface surfaces and/or (b) the connector comprises a thin window (22), since a pressure applied by the male interface surface (7*i*) onto the window could break the window. Absent a window, it is also possible to make without a support surface (3*s*) resting on the shoulder (30*s*) and to ensure contact between the male and female interface surfaces by driving the male tip unit all the way through the cavity until the male interface surface contacts the female interface surface, without of damaging any component of the connector.

In a preferred embodiment, the at least one optics bore portion (33*b*) is offset with respect to the first longitudinal axis, Z1. This is necessarily the case if the female component comprises more than one optical component which are not concentric. Similarly, the at least one male through-bore (7*b*) is offset with respect to the second longitudinal axis, Z2. This is necessarily the case if the male component comprises more than one optical fibre. In these conditions, the female and male elements must be coupled such that the male tip fits in the cavity with a finite number of azimuthal angles only, and such that at any of said finite number of azimuthal angles, one or more optical elements in the at least one optics bore portion (33*b*) face the optical fibre (41*f*) inserted in the at least one male through-bore (7*b*), within a tolerance preferably of less than ±50 µm, preferably of less than ±30 µm. Note that, on the one hand, one optic bore portion may face more than one male through-bore (e.g., if an optical component has a diameter encompassing two optical fibres inserted in adjacent tip through bores. On the other hand, one through bore can face more than one optical component, e.g., if two optical components are placed side by side or concentrically.

As illustrated in FIG. 2, such tight tolerances of less than ±50 µm, preferably of less than ±30 µm are justified by the light energy drop of the light energy transferred from a light source to an optical fibre in coupled position observed for a misalignment, d(OF-L) between the light source and optical fibre, higher than 50 µm. In order to limit the number of azimuthal angles allowing the male and female components to be coupled, the following alternative or concomitant solutions can be applied.

In a first embodiment, the cavity has a cavity cross-section normal to the first longitudinal axis, Z1, defining a non-revolution geometry at least over a portion of the depth of the cavity. The male tip (7w) and the male interface surface (7i) also have a non-revolution geometry with respect to the second longitudinal axis, Z2, mating the non-revolution geometry of the cavity cross-section, such that the male tip fits in the cavity with a finite number of azimuthal angles only, within the required tolerances.

In an alternative embodiment, the coupling bore portion has a coupling bore cross-section normal to the first longitudinal axis, Z1, defining a non-revolution geometry at least over a portion of a depth of the coupling bore portion. The washer portion (3w) also has a non-revolution geometry with respect to the second longitudinal axis, Z2, mating the non-revolution geometry of the coupling bore cross-section, such that the washer portion fits in the coupling bore portion with said finite number of azimuthal angles only, such that the washer portion fits in the coupling bore portion with said finite number of azimuthal angles only, such that at any of said finite number of azimuthal angles the at least one optics bore portion (33b) faces the at least one tip through bore, within a tolerance preferably of less than ±100 μm, more preferably of less than ±70 μm.

The foregoing two embodiments can be combined, for example, with the coupling bore cross-section and the washer portion (3w) having non-revolution geometries within a first tolerance to engage the male component into the female component with a generally correct azimuthal angle, and with the cavity cross-section and the male tip (7w) and the male interface surface (7i) having non-revolution geometries within a second tolerance, lower than the first tolerance, for ensuring n optimal azimuthal angle, yielding a misalignment of preferably less than ±50 μm or less than ±30 μm.

Such embodiments are particularly suitable for optical fibres connectors wherein the female component comprises more than one coupling bore portions (33b), and wherein the male component comprises more than one male through-bore s (7b). The finite number of azimuthal angles such that each male through-bore faces at least one corresponding optics bore portion (33b), within the tolerance is equal to or lower than the degree of axial symmetry of the arrangement of optical fibres and optical elements with respect to the first and second longitudinal axes, Z1, Z2.

For example, as shown in FIGS. 8(c) & (d), in case two optical fibres are arranged symmetrically on either side of the second longitudinal axis, Z2, with a degree of symmetry of two. The finite number of azimuthal angles can therefore be one or two. In the embodiment of FIG. 8(a), only one azimuthal angle is possible, because the two protrusions (3a) of the washer—and corresponding recesses (30a) of the coupling bore portion have different geometries. A finite number of two would have been obtained if both protrusions (3a) (and recesses (30a)) were identical. It is clear that the number of protrusions can vary from one to as many as considered necessary for limiting the number of allowed azimuthal angles between the male and female components.

FIG. 9(a) shows a combination of three fibres homogeneously distributed around the second longitudinal axis, Z2, yielding a degree of symmetry of three. The male element (M) illustrated in FIG. 9(a) comprises a combination of non-revolution elements (3a, 7a) in both washer unit (3) and male tip unit (7). The washer comprises two protrusions or wings (3a) of different geometries, allowing a single azimuthal angle of coupling. The coupling bore portion (30b) comprising mating recesses (not shown). The tolerance between the geometries of the wings (3a) and the recesses (30a) (not shown) is not critical as they only serve to pre-orientate the male component with the correct azimuthal angle with respect to the female component.

The male tip itself can have a non-revolution geometry thus restricting the number of allowed azimuthal angles between the male and female components. Alternatively, as shown in FIG. 9(a), the male tip unit (7) may have a geometry generally of revolution. It can then comprise a non-revolution element in the form of a recess (7a) (or protrusion) which mates a corresponding protrusion (31a) (or recess) shown in FIG. 9(b) with a much tighter tolerance than required by the washer unit/coupling bore portion system discussed supra, yielding a misalignment between the three optical fibres (41f) of the male element with respect to the corresponding optical elements (21L, 21s, 22L) of the female component (F) of less than ±50 μm, preferably less than ±30 μm.

The foregoing configurations allow a reproducible connection between male and female components to be achieved with excellent alignment of a set of corresponding optical fibres and optical elements, even in cases wherein at least one thereof is offset with respect to the first and second longitudinal axes, Z1, Z2.

Coupling Component (C)

One of the key features of the present invention is the coupling component (C) for fixing the female (F) and male (M) components in their coupled position. The coupling component of the present invention must comprise one or more elements including at least one rotatable element (40r) being rotatable about the first and/or second longitudinal axes, Z1, Z2, with respect to a fixed element (40f) of the male or female component. All optical fibres (41f) and optical elements coupled to the connector must remain static upon rotation of the rotatable element. In other words, they must not rotate together with the rotatable element (40r). Rotation of the rotatable element with respect to the fixed element reversibly locks the male and female components in the coupled position.

In order to facilitate the coupling of the male and female components of the optical fibres connector by a surgeon during an implantation operation, neither the female component nor male component comprises any loose part, and all elements of the coupling component are attached to the male and/or female components. This way, there is no risk of losing a part of the AIMD into the open body of a patient during operation. For example, the connector described in WO2018068807 comprises several loose parts, including screws and washers, all elements of small dimensions which can easily be lost during operation. The present invention clearly solves this critical issue.

Because during an implantation operation, the electrode unit (60) is generally implanted first and the end of the optical unit (41) provided with the male component of the optical fibres connector is driven from the implantation location of the electrode unit to the implantation location of the encapsulation unit (50) subcutaneously through a guide, the male component (and any element of the coupling component attached thereto) has a dimension normal to the second longitudinal axis, Z2, inscribed in a circle having a diameter of not more than 15 mm, preferably of not more than 10 mm, and more preferably of not more than 7 mm. The reduction of said diameter allows guides of smaller diameters to be used, which is less traumatic for the patient.

The geometry of the optical fibres connector of the present invention does not require any protrusions sticking out of the connector. A connector with smooth outer surfaces also facilitates the passage of the connector through the guide.

Some specific coupling components are discussed below, including: (a) nut-screw types, (b) bayonet-types, and (c) key-lock types. All of the foregoing types can further be provided with snap-fitting elements, for indicating that the coupled position has been reached and/or for securing the rotatable element (40r).

Nut-Screw Type Coupling Component

FIGS. 1(b) & (c), 3, 4, 7, and 8 depict nut-screw type coupling components (C) suitable for the present invention. In a nut-screw type coupling component the rotatable element (40r) comprises a rotatable nut provided with a rotatable thread (40rt) and the fixed element comprises a screw provided with a fixed thread (40ft), mating the rotatable thread of the nut.

FIGS. 1(b) & (c), 3, and 7 illustrate embodiments of the present invention provided with a nut-screw coupling element wherein the rotatable element/nut (40r) is mounted on the male component (M). The fixed element/screw (40f) is provided in the female component; connections are illustrated to a further optical fibre in FIG. 3 and to an encapsulation unit in FIG. 7. The fixed thread (40ft) of the fixed element/screw (40f) of the female components (F) of FIGS. 3 and 7 is internal, i.e., facing the interior of the coupling bore portion. The corollary is that the rotatable thread (40rt) of the rotatable element/nut (40r) is external, i.e., facing outwards, to meet the fixed thread of the fixed element/screw. It is clear that the reverse design can be applied instead, with the fixed element/screw comprising an external fixed thread and the rotatable element/nut comprising an internal rotatable thread.

Figure 4B:
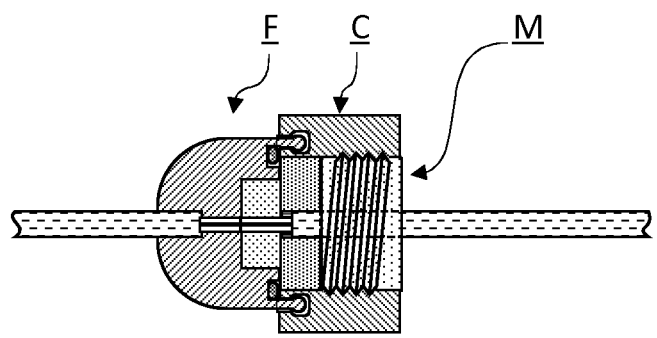

FIGS. 4 & 8 illustrate embodiments of the present invention provided with a nut-screw coupling element wherein the rotatable element/nut (40r) is mounted on the female component (F). The fixed element/screw (40f) is provided in the male component (M): a connection to a further optical fibre is illustrated in FIG. 4 and to an encapsulation unit in FIG. 8. Here the fixed threads (40ft) of the fixed elements/screws of the male components (M) of FIGS. 4 and 8 are external, and the rotatable thread (40rt) of the rotatable element/nut (40r) in the female component is internal. It is clear that the reverse design can be applied instead, with the fixed elements/screws comprising an internal fixed thread (40ft) and the rotatable element/nut comprising an external rotatable thread (40rt).

The relative lengths of the rotatable element/nut and of the fixed element/screw measured along the first and second longitudinal axes, Z1, Z2, must be suitable so that when the nut is tightly screwed onto the screw, a pressure surface of the rotating element forces the support surface (3s) of the washer to rest in tight contact on the shoulder (30s) of the receiving portion. This way, upon feeling a resistance of the nut to further rotation, the surgeon knows that the coupling between the male and female components is effective and is stabilized with the coupling component consisting of a nut and a screw.

The rotation of the rotatable element/nut can be carried out as is usual in the art with a tool, such as a spanner, engaged in a polygonal external surface of the nut, as visible in FIGS. 3, 4, 7, and 8.

In order to prevent a tightly screwed nut from getting loose with time, due to vibrations and other movements of the implanted AIMD, a snap-fitting element can be added. An example of snap-fitting element is illustrated in FIG. 7(c), showing a surface of the nut being provided with protrusions and the fixed element being provided with mating recesses (or the other way round), such that the protrusions interact resiliently with the recesses when the nut is tightly screwed, and the male and female components are in the coupled position. The snap-fitting element prevents the nut from freely rotating and thus from loosening the grip between male and female components. Furthermore, the snap related with the resilient interaction is also indicative to the surgeon that the male and female components are fixed in their coupled position.

To summarize, the nut can rotate about and translate along the second or first longitudinal axis, Z2, Z1, depending on whether it is mounted on the male or female component, respectively. Since neither the female component nor the male component comprises any loose part, the nut cannot be removed from the male or female element (at least not without a specific effort to this effect). The rotatable thread (40rt) can be engaged into the fixed thread when the male tip (7w) is engaged in the cavity. The rotation of the nut over the fixed thread translates the washer portion along the coaxial first and second longitudinal axes, Z1, Z2, towards the female interface surface, until the support surface (3s) of the washer contacts the shoulder (30s) of the female component.

Bayonet Type Coupling Component

An alternative coupling component (C) is of the bayonet type. A bayonet type coupling component comprises one more pins (40pn) and corresponding matching slots of defined geometries allowing the insertion of the one or more pins into corresponding slots upon bringing the male and female components into their coupled position and locking of the two components by relative rotation of the pins and slots with respect to one another.

FIG. 5 illustrates an embodiment of bayonet coupling component, wherein the pins (40pn) are oriented radially and outwardly with respect to the first or second longitudinal axis, Z1, Z2. It is clear that the pins may extend inwardly, instead. The slots are L-shaped and opened at one end for allowing the insertion of a corresponding pin as the male and female components are brought into their coupling position. In FIG. 5, the pins are provided on the fixed element and the slots are provided on the rotatable element (40r), but the reverse construction is also possible with the pins in the rotatable element and the slots in the fixed element. Similarly, the rotatable element (40r) is mounted on the male component, but it is clear that it could be mounted on the female component instead. The rotatable element can rotate relative to all the remaining components of the system, including the optical unit (41) coupled thereto.

The male and female components can be brought into the coupled position by translation along the coaxial first and second longitudinal axes, Z1, Z2, with each pin penetrating into a first segment of a corresponding L-shaped slot through its open end, said first segment being parallel to the first and second longitudinal axes, Z1, Z2. When the pins reach the ends of the corresponding first segments, the rotatable element (40r) can be rotated so that the pins engage into a second segment of the slots extending transverse to the first segment, thus locking the male and female components in their coupled position. If the second segment of the L-shaped slot forms an angle of 90° with the first segment, the rotation of the rotatable element locks the male and female components in their respective positions they had when the pins reached the end of the first segment, without translation along the first or second longitudinal axis, Z1, Z2. If the angle between the first and second segments of the slots is larger than 90°, then the rotation of the rotatable element also drives a further relative translation between the male and female components along the first and second longitudinal axes, Z1, Z2, pressing the support surface (3s) of the washer against the shoulder (30s) of the female component. The relative positions of the male and female components can thus be controlled with much accuracy and reproducibility.

As discussed with respect to the nut-screw coupling components supra, a snap-fit device can be provided to prevent the rotating element (40r) from freely rotating and thus from loosening the grip between male and female components, and for indicating to the surgeon that the male and female components are locked in their coupled position. For example, a protrusion (not shown) can be provided in the second segment of the L-shaped slot, adjacent to a closed end thereof, at a position beyond which the pin sets the male and female components in the coupled position.

Key-Lock Type Coupling Component

A key-lock type coupling component comprises a key having a non-revolution geometry, and a keyhole having a geometry allowing insertion of the key into the keyhole with a limited number of azimuthal angular positions of the key with respect to the keyhole and allowing locking of the inserted key upon relative rotation of the keyhole and the key.

FIGS. 6(a) & (b) illustrate a first embodiment of key-lock coupling component. The key is formed by the washer portion (3w) and the non-revolution elements of the washer portion in the form of the two protrusions (3a) visible in FIGS. 6(a) & (b). The keyhole is formed by a rotatable element (40r) provided with an opening forming the keyhole opening and having recesses (40a) mating the protrusions (3a) of the washer. Because the two protrusions (3a) and corresponding recesses (40a) have different geometries, the key can be inserted into the keyhole opening with a single azimuthal angular orientation. This allows the male component to be inserted into the female component with approximately the correct angular position required by the coupling position. As illustrated in FIG. 6(a), the male component can be inserted into the keyhole in the right angular orientation and pushed all the way until the support surface (3s) of the washer contacts the shoulder (30s) of the female component. The rotation of the rotatable element (40r) locks the male and female components in the coupling position as follows.

The fixed element (40f) is rigidly fixed to the female (or male) component. The rotatable component is rotatably coupled to the fixed element. As illustrated in FIG. 6(b), by rotating the rotatable component about the first longitudinal axis, Z1, the recesses (40a) of the keyhole opening become offset with respect to the protrusions (3a) of the washer portion and the male component is locked in its coupling position. The rotatable element applies a pressure onto the protrusions (3p) of the washer portion (3w) thus locking the male and female components in the coupled position. If the surface of the rotatable element in contact with the protrusions (3p) of the washer is slanted with respect to (i.e., not normal to) the first longitudinal axis, the rotation of the rotatable element can also serve to drive the translation of the male component further into the female component to force the support surface (3s) of the washer against the shoulder (30s) of the female component.

As shown in FIGS. 6(a) & (b) the rotatable element is provided with snap-fitting devices (40s) formed by protrusions formed at a free end of resilient levers. The resilient deformation of the levers allows the rotatable element to freely rotate until the protrusions reach recesses provided in the fixed element. At this point, the resilient levers are so biased that the protrusions engage into the recesses, thus blocking the rotation of the rotatable element. The male component is thus safely locked to the female component in the coupling position. Other designs of snap-fitting devices than illustrated in FIGS. 6(a) & 6(b) can be envisaged and are known to a person of ordinary skills. For example, instead of extending radially, the protrusions and recesses can extend parallel to the first longitudinal axis, Z1. The number of snap-fitting devices can also vary as shown in FIGS. 6(c) & (d).

FIGS. 6(c) & (d) illustrates a second embodiment of a key-lock coupling component. Like for the first embodiment discussed supra with respect to FIG. 6(a)-6(b) the key is formed by the washer portion (3w) and the non-revolution elements of the washer portion in the form of the two protrusions (3a) visible in FIGS. 6(c) & (d). The keyhole is also formed by a rotating element (40r) provided with an opening forming the keyhole opening and having recesses (40a) mating the protrusions (3a) of the washer. The coupling component of the second embodiment differs from the first embodiment in that the coupling component comprises bean shaped slots (40sl) which have a circular geometry centred on the first longitudinal axis, Z1, and have an insert end, and a locking end opposite the insert end. The rotatable element is rotatably mounted to a fixed element of the female component. The coupling component comprises pins, each inserted in a corresponding bean-shaped slot, such that the rotatable element can be rotated about the first longitudinal axis, Z1, such that the pin contacts the insert end where the keyhole opening is at an insertion position at which the key can be inserted into the keyhole opening, and the locking end of the corresponding bean-shaped slot where the key is locked in the keyhole opening and cannot be removed therefrom. The rotational movement can be seen by comparing the left-hand side views of FIG. 6(c) (=insert end) and FIG. 6(d) (=locking end). In FIGS. 6(c) & (d), the pins are part of the rotatable element (40r) and the bean-shaped slots are part of the fixed element (40f). It is clear that the design can be inverted very easily, by providing the bean-shaped slots in the rotatable element and by fixing the pins to the fixed element.

As illustrated in FIG. 6(c), the male component can be inserted into the keyhole at the right angular orientation and pushed all the way until the support surface (3s) of the washer portion contacts the shoulder (30s) of the female component. The rotation of the rotatable element (40r) locks the male and female components in the coupling position in a similar manner as discussed with respect to the first embodiment illustrated in FIGS. 6(a) & 6(b). Here too, if the surface of the rotatable element in contact with the protrusions (3p) of the washer is slanted with respect to (i.e., not normal to) the first longitudinal axis, the rotation of the rotatable element can also serve to drive the translation of the male component further into the female component to force the support surface (3s) of the washer against the shoulder (30s) of the female component.

The pins are preferably mushroom shaped, comprising a stem rigidly coupled at a first end to the rotatable (or the fixed) element, and inserted in the bean-shaped slot. It comprises a head at a second end of the stem, opposite the first end, and extending outwardly radially. The width of a bean-shaped slot measured radially is larger than a diameter of the stem of the pin, to allow free movement of one relative to the other, and is smaller than the head of the mushroom, to prevent the rotatable element from falling loose off the female component.

Here again, a snap-fitting device can be provided to ensure that the male and female components are in the coupling position, and that they are securely locked in said coupling position. For example, as shown in FIG. 6(d) (B-B cut), the snap-fitting device (40s) can be formed by a protrusion formed at a free end of a resilient lever. The resilient deformation of the lever allows the rotatable element to freely rotate until the protrusion reaches a recess provided in the fixed element. At this point, the resilient lever is so biased that the protrusion engages into the recess, thus blocking the rotation of the rotatable element. The male component is thus safely locked to the female component in the coupling position.

Alternatively, as shown in the inset of FIG. 6(c), a protrusion can extend inward radially close to the locking end of the bean-shaped slot, restricting the width of the slot at said point to restrict the movements of the stem of the pin. By correctly dimensioning said protrusion and by a proper selection of the flexibility thereof, the rotatable element can be rotated until the stem of the pin hits the protrusion. By forcing slightly, the rotatable element can be further rotated until the stem reaches the locking end of the bean-shaped slot. The surgeon thus knows the coupling is effective and is securely locked.

Summary and Advantages

The optical fibres connectors according to the present invention are of simple and cost-effective construction. They are reliable and durable, and easier to use by a surgeon than hitherto possible. Optical fibres coupled to the male component of the connector can be aligned with great accuracy with optical elements, including optical fibres, sources of light, or light sensors (or photodetectors), coupled to the female component of the connector. Alignments within a tolerance of the order of less than ±50 µm are easily achieved, and tolerances of less than ±30 µm, or less than ±15 µm, or less than ±10 µm are also possible, thus yielding a highly energy efficient optoelectronic AIMD.

Such tight tolerances are also made possible thanks to the construction of the male component comprising a male tip (7), provided with a male tip through bore. An optical fibre is inserted into the male through-bore with the proximal end thereof sticking out of the male interface surface. If several optical fibres (41f) are comprised in an optical unit (41), all the optical fibres can likely be inserted into a corresponding male through-bore with their proximal ends sticking out of the male interface surface. They can all be cut together approximately flush with the male interface surface, and then polished all together to yield a perfectly smooth male interface surface with proximal ends of the optical fibres perfectly flush with said surface. This is very important to control the axial distance of the proximal ends of the optical fibres to the optical elements when the male and female components are in the coupled position. The preparation of the male component is easy, repeatable, and very accurate. The same of course applies to the female component if it is coupled to optical fibres.

Once the female and male components are ready, the surgeon can implant the electrode unit (60) onto the tissue to be treated and run the optical unit through a guide to the location of implantation of the encapsulation unit. Because the male component has very small dimensions, the guide can be finer than otherwise required with larger connectors. Absent any loose part, such as screws, washers, nuts, etc., the surgeon cannot lose any part in the patient body during manipulation of the connector. Bringing the male and female components into the coupled position is very easy. Locking the male and female components in the coupled position is achieved simply by rotation of the rotatable element (40r) with or without a tool, such as a spanner. The locked coupled position can further be secured with a snap-fitting device.

With the design of the support surface (3s) of the washer resting against the shoulder (30s) of the female component, and with the easily polished proximal ends of the optical fibres, the distance of the proximal ends of the optical fibres to the optical elements is repeatedly achieved with great accuracy and with no particular action required by the surgeon. In case an optical fibre is offset with respect to the second longitudinal axis, Z2, the azimuthal angle required by the coupling position such that the offset optical fibre accurately faces a corresponding optical element can easily be controlled with a non-revolution element of the male tip unit and optionally of the washer. Again, the surgeon cannot make a mistake as said non-revolution elements permit the bringing of the male and female components into the coupled position only with the limited number of azimuthal angles required to have a perfect alignment of the optical fibres with the optical elements. The surgeon does not need to make trials and errors and can repeatedly achieve a secure connection with perfect alignment.

By ensuring that the rotation of the rotatable element with respect to the fixed element drives a translation of the male component along the coaxial longitudinal axes, Z1, Z2, towards the female component, it is made even easier to ensure that the male component has reached the coupled position, with the support surface (3s) of the washer contacting the shoulder (30s) of the female component.

| Ref# | Reference |
|---|---|
| 3 | Washer unit |
| 3a | Non-revolution element of the washer (e.g., protrusion or recess) |
| 3b | Male through-bore |
| 3d | Washer outlet |
| 3p | Washer back surface |
| 3u | Washer inlet |
| 3s | Washer support surface |
| 3w | Washer portion |
| 7 | Male tip unit |
| 7a | Non-revolution element of the male tip unit (e.g., protrusion or recess) |
| 7b | Tip through bore |
| 7c | Coupling portion of the male tip unit |
| 7d | Tip outlet |
| 7i | Male interface surface |
| 7u | Tip inlet |
| 7w | Male tip |
| 8 | Sleeve |
| 8o | Protective sheath |
| 10 | Male support element |
| 21b | Board supporting the sources of light emission and/or light sensors |
| 21L | Source of light emission |
| 21s | Light sensor |
| 21x | Lens |
| 22 | Window |
| 22L | Micro-optics element (e.g., lens) |
| 22i | Window inner surface |
| 22o | Window outer surface |
| 30 | Female support element |
| 30a | Non-revolution element of the coupling bore portion (e.g., recess or protrusion) |
| 30b | Coupling bore portion |
| 30c | Bore locking end |
| 30e | Support locking end |
| 30i | Female interface surface |
| 30o | Bore optics end |
| 30s | Bore shoulder |

-continued

| Ref# | Reference |
|---|---|
| 31 | Cavity |
| 31a | Non-revolution element of the cavity (e.g., protrusion or recess) |
| 32 | Receiving portion |
| 33b | Optics bore portion |
| 33e | Support optics end |
| 33o | Optics bore end |
| 35 | Retaining means for retaining the rotatable element |
| 37 | Female tip unit |
| 40a | Keyhole opening of rotatable element (40r) |
| 40f | Fixed element of the coupling component C |
| 40ft | Fixed thread of the fixed element |
| 40p | Pressure surface of rotating element |
| 40pn | Pin |
| 40r | Rotatable element of the coupling component C |
| 40rt | Rotatable thread of the rotatable element |
| 40s | Snap-fit element |
| 40sl | Slot |
| 41 | Optical unit |
| 41f | Optical fibre |
| 41p | Optical fibre proximal end |
| 50 | Encapsulation unit |
| 50d | Optical detector |
| 50h | Housing |
| 50L | Source of light emission |
| 60 | Electrode unit |
| C | Coupling component |
| F | Female component |
| M | Male component |
| Z1 | First longitudinal axis |
| Z2 | Second longitudinal axis |

The invention claimed is:

1. An optical fibres connector for an optoelectronic active implantable medical device (AIMD) for implantation in a living body, said optical fibres connector comprising a female component (F), a male component (M), and a coupling component (C), wherein:

(A) the female component (F) comprises:
(a) a female support element (30) comprising a support locking end (30e) and a support optics end (33e), said female support element being provided with,
a coupling bore portion (30b) extending along a first longitudinal axis, Z1, between a bore locking end (30c) and a bore optics end (30o), said coupling bore portion comprising
a receiving portion (32) opening at the support locking end and forming at an opposite end a shoulder (30s) surrounding,
a cavity (31) adjacent to the receiving portion of given depth, d, measured along the first longitudinal axis, Z1, and ending at the bore optics end forming a female interface surface, and
at least one optics bore portion (33b) extending parallel to the first longitudinal axis, Z1, from an optics bore end (33o) opening at the support optics end, and either,
to an opening at the female interface surface, thus defining at least one female through-bore extending from the support optics end to the support locking end, or
to an inner surface (22i) of a window (22) separated from the cavity by a thickness of the window (22) comprising an outer surface (22o), wherein said window is transparent to selected light wavelengths range,
(b) one or more optical elements selected from,
at least one optical fibre (41f) comprising an optical fibre proximal end (41p), and being inserted in the corresponding at least one optics bore portion (33b), such that the optical fibre proximal end is at a predefined distance from the female interface surface of the cavity, and is preferably flush with said female interface surface or is preferably in contact with the inner surface of the window, or
at least one source of light emission (21L) and/or light sensor (21s), facing the inner surface (22i) of the window (22)

(B) the male component (M) comprises a male support element (10) comprising:
(a) a washer portion (3w) comprising at least one male through-bore (3b) extending parallel to a second longitudinal axis, Z2, from a washer inlet (3u) opening at a back surface (3p) to a washer outlet (3d) opening at a support surface (3s) of the washer portion, said washer portion having a geometry allowing insertion thereof into the coupling bore portion (30b) of the female support element until the support surface contacts the shoulder (30s) of the female component,
(b) a male tip (7w) coupled to the support surface of the washer portion, and comprising,
a male interface surface (7i) having a geometry mating the cavity geometry, such that the male tip snugly fits in the cavity,
one or more male through-bores (7b) extending parallel to the second longitudinal axis, Z2, from a tip inlet (7u) in fluid communication with the 0 at least one male through-bore (3b) to a tip outlet (7d), opening at the male interface surface (7i),
an optical fibre (41f) inserted in each of the one or more male through-bores (7b), and comprising an optical fibre proximal end (41p), which is at a predefined distance from the tip outlet (7d), preferably flush 5 with the tip outlet, (C) a coupling component (C), for reversibly locking the male and female components in a coupled position, wherein the coupled position is defined by the male component being coaxially inserted in the receiving portion of the female component with the first and second longitudinal axes, Z1 and Z2, being coaxial and with the support surface (3s) of the washer resting on the shoulder (30s) of the receiving portion, and with the male tip unit being fitted in the cavity,
with the male interface surface (7i) being located at a predefined distance measured along the longitudinal axis, Z2, from the female interface surface (30i), preferably in contact with one another,
the proximal ends of the one or more optical fibres of the male element are in perfect alignment with the one or more optical elements of the female component, characterized in that,
the coupling component comprises a fixed element (40f) and a rotatable element (40r) being rotatable about the first and/or second longitudinal axis, Z1, Z2, with respect to the fixed element (40f), all optical fibres (41f) and optical elements of the connector remaining static upon rotation of the rotatable element,
reversibly locking the male and female components in the coupled position is 5 achieved by rotating the rotatable element with respect to the fixed element, both female component and male component comprise no loose part, and all elements of the coupling component are attached to the male and/or female components the male component and any element of the coupling component attached thereto have a dimension normal to the second longitudinal axis, Z2, inscribed in a circle having a diameter of not more than 15 mm.

2. The optical fibres connector according to claim 1, wherein, at least one or more optical elements are offset with respect to the first longitudinal axis, Z1, the at least one optical fibre inserted in a male through-bore (7b) is offset with respect to the second longitudinal axis, Z2, the cavity has a cavity cross-section normal to the first longitudinal axis, Z1, defining a non-revolution geometry at least over a portion of the depth of the cavity, the male tip (7w) and the male interface surface (7i) have a non-revolution geometry with respect to the second longitudinal axis, Z2, mating the 5 non-revolution geometry of the cavity cross-section, such that the male tip fits in the cavity with a finite number of azimuthal angles only, and such that at any of said finite number of azimuthal angles, one or more optical elements of the female component face the optical fibre (41f) inserted in the at least one male through-bore (7b), within a tolerance preferably of less than ±50 µm.

3. The optical fibres connector according to claim 1, wherein, at least one or more optical elements are offset with respect to the first longitudinal axis, Z1, the at least one optical fibre inserted in a male through-bore (7b) is offset with 5 respect to the second longitudinal axis, Z2, the coupling bore portion has a coupling bore cross-section normal to the first longitudinal axis, Z1, defining a non-revolution geometry at least over a portion of a depth of the coupling bore portion, the washer portion (3w) has a non-revolution geometry with respect to the second longitudinal axis, Z2, mating the non-revolution geometry of the coupling bore cross-section, such that the washer portion fits in the coupling bore portion with said finite number of azimuthal angles only, such that at any of said finite number of azimuthal angles one or more optical elements of the female component face the optical fibre (41f) inserted in the at least one male 5 through-bore (7b), within a tolerance preferably of less than ±100 µm.

4. The optical fibres connector according to claim 2, wherein, the female component comprises more than one optical component, the male component comprises more than one male through-bores (7b) supporting an optical fibre, the male and female components being arranged in the coupled position such that at any of said finite number of azimuthal angles each optical fibre faces at least one corresponding optical element.

5. The optical fibres connector according to claim 1, wherein, the female support element is monolithic or, alternatively, comprises multiple components, including a coupling unit (38) comprising the receiving portion of the bore, the coupling unit being preferably made of a polymeric material or metal, and a female tip unit (37) comprising the cavity and the one or more fibre 5 through-bores (33b) or the window (22), the male support element is monolithic or, alternatively, comprises multiple components, including:

a washer unit (3) forming the washer portion and a male tip unit (7) forming the male tip and comprising a male tip unit coupling portion (7c) for coupling to the support surface (3s) of the washer portion.

6. The optical fibres connector according to claim 1, wherein the male component (M) comprises a sleeve (8) integral with or coupled to the back 5 surface of the washer portion (3w) and comprising at least a sleeve bore coaxial with the at least one male through-bore (3b) of the washer portion and forming together at least one single bore extending along the second longitudinal axis, Z2, from a sleeve inlet to the washer outlet (3d), and wherein the washer portion (3w) forms a flange extending outwardly over a perimeter of the washer outlet (3d).

7. The optical fibres connector according to claim 1, wherein the female component (F) is part of an encapsulation unit (50), wherein the encapsulation unit comprises a housing (50h) defining an inner space sealed from an outside of the housing, wherein the inner surface (22i) of the window (22) belongs to the inner space and the outer surface (22o) of the window faces 5 the outside, the at least one optical element is located in the inner space, facing the inner surface of the window, and is preferably mounted on a board (21b) supporting the at least one optical element at a predefined distance from the inner surface of the window and at a predefined azimuthal angle about the first longitudinal 5 axis, Z1, such that, in the coupled position, each optical component faces at least one corresponding male through-bore (7b) or each through bore (7b) faces at least one optical element, within the tolerance, one or more components selected from a source of electric power, or an analogue and/or digital circuit, are contained in the inner space.

8. The optical fibres connector according to claim 1, further comprising at least one sealing element (11), including one sealing element sitting on the shoulder (30s) of the coupling bore portion (30b) and enclosing a circumference of the cavity, said sealing element sealing the female interface surface of the cavity from an outside environment, when the male and female components are locked in the coupled position.

9. The optical fibres connector according to claim 1, wherein the coupling component is of a nut-screw type, wherein:

the fixed element (40f) of the coupling component comprises a fixed thread (40ft) centred on the first or second longitudinal axis, Z1, Z2, and is located on the female or the male component, respectively, and wherein the rotatable element comprises a nut provided with a rotatable thread (40rt) mating the fixed thread (40f), and mounted on the male or the female element, respectively, wherein the nut can rotate about and translate along the second or first longitudinal axis, Z2, Z1, respectively, the nut cannot be removed from the male or female component, the rotatable thread can be engaged into the fixed thread when the male tip (7w) is engaged in the cavity, and wherein the rotation of the nut over the fixed thread translates the washer portion along the coaxial first and second longitudinal axes, Z1, Z2, towards the female interface surface, until the support surface (3s) of the washer contacts the shoulder (30s) of the female component.

10. The optical fibres connector according to claim 1, wherein the coupling component is of a bayonet type, comprising:
- one or more pins (40pn) extending radially out of one of the fixed or rotatable element,
- a corresponding number of L-shaped slots (40sl) provided on the other of the fixed or rotatable element comprising the one or more pins, wherein each 5 L-shaped slot comprises a first segment extending from an open end parallel to the first or second longitudinal axis, Z1, Z2, and a second segment extending transverse to the first segment to a closed end, and preferably forming an angle of at least 90° with the first segment, wherein
- as the male and female components are brought into the coupled position by translation along the coaxial first and second longitudinal axes, Z1, Z2, each pin engages into the first segment of the corresponding L-shaped slot until it reaches the second segment, and wherein
- the male and female components are locked in their coupled position by rotation of the rotatable element (40r), thus running each pin along the second segment of the corresponding L-shaped slot.

11. The optical fibres connector according to claim 1, wherein the coupling component is of a key-lock type, wherein:
- the washer (3w) has a non-revolution geometry and comprises one or more protrusions (3p) extending outwards and radially with respect to the second longitudinal axis, Z2,
- the rotatable element comprises a keyhole opening normal to the first longitudinal axis, Z1, and comprising one or more recesses (40a) mating the one or more protrusions (3p) of the washer, such that the washer can be inserted through the keyhole opening with a limited number of azimuthal angles, wherein
- as the male and female components are brought into the coupled position by translation along the coaxial first and second longitudinal axes, Z1, Z2, the washer is inserted through the keyhole opening, until the support surface (3s) of the washer contacts the shoulder (30s) of the female component,
- the male and female components are locked in their coupled position by rotation of the rotatable element (40r), thus offsetting the one or more recesses with respect to the corresponding one or more protrusions of the washer.

12. The optical fibres connector according to claim 1, wherein the rotation of the rotatable element with respect to the fixed element drives a translation of the male component along the coaxial longitudinal axes, Z1, Z2, towards the female component, until the support surface (3s) of the washer contacts the shoulder (30s) of the female component.

13. The optical fibres connector according to claim 1, wherein the coupling component comprises a snap-fitting element (40s) comprising a resilient lever provided with a protrusion, wherein the rotatable element can rotate with the resilient lever in a biased configuration, until the protrusion reaches a corresponding recess in which it can engage thus releasing the biased configuration and reaching a snapped position.

* * * * *